(12) United States Patent
Uzawa

(10) Patent No.: US 8,243,129 B2
(45) Date of Patent: Aug. 14, 2012

(54) OBJECTIVE LENS AND ENDOSCOPE APPARATUS

(75) Inventor: Tsutomu Uzawa, Hidaka (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/135,259

(22) Filed: Jun. 29, 2011

(65) Prior Publication Data

US 2012/0007972 A1 Jan. 12, 2012

Related U.S. Application Data

(63) Continuation of application No. PCT/JP2010/070482, filed on Nov. 17, 2010.

(30) Foreign Application Priority Data

Dec. 7, 2009 (JP) ................................ 2009-277845
Sep. 14, 2010 (JP) ................................ 2010-205897

(51) Int. Cl.
*A62B 1/04* (2006.01)
*G02B 21/02* (2006.01)

(52) U.S. Cl. .......... 348/65; 359/656; 359/657; 359/658; 359/659; 359/660; 359/661; 359/749; 359/750; 359/751; 359/752; 359/753; 359/754; 359/755; 359/756; 359/771

(58) Field of Classification Search .......... 359/656–661, 359/771, 781, 763, 770, 749–756, 740; 348/335, 348/343, 344, 345, 240.3, 65; 396/72, 79, 396/85

See application file for complete search history.

(56) References Cited

U.S. PATENT DOCUMENTS

| 6,844,991 B2 | 1/2005 | Mizuguchi |
| 2004/0021958 A1 | 2/2004 | Mizuguchi |
| 2005/0094286 A1 | 5/2005 | Mizuguchi |
| 2006/0203361 A1 | 9/2006 | Kato |

FOREIGN PATENT DOCUMENTS

| JP | 09-297264 | 11/1997 |
| JP | 10-020189 | 1/1998 |
| JP | 2004-029282 | 1/2004 |
| JP | 2004-258515 | 9/2004 |
| JP | 2006-251272 | 9/2006 |
| JP | 3140304 | 3/2008 |

*Primary Examiner* — Mehrdad Dastouri
*Assistant Examiner* — Kristin Dobbs
(74) *Attorney, Agent, or Firm* — Kenyon & Kenyon LLP

(57) ABSTRACT

An objective lens includes, in order from an object side, a front group having negative refractive power, an aperture stop, and a rear group having positive refractive power, wherein the front group includes, in order from the object side, a first lens which is a negative meniscus lens with a convex surface turned to the object side and a second lens which is a negative lens with a concave surface turned to the object side; the rear group includes, in order from the object side, a positive third lens and a fourth lens made up of a positive lens and a negative lens cemented together, and the objective lens satisfies conditional expression (1) below:

$$-0.8 < f\_F/f\_R < -0.3 \qquad (1),$$

where $f\_F$ is a focal length of the front group, and $f\_R$ is a focal length of the rear group.

5 Claims, 20 Drawing Sheets

FIG.1

| EXAMPLE NO. | | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| FOCAL LENGTH OF ENTIRE SYSTEM | FL | 1.000 | 1.000 | 1.000 | 1.000 | 1.000 | 1.000 | 1.000 | 1.000 | 1.000 | 1.000 | 1.000 | 1.000 | 1.000 | 1.000 |
| F-NUMBER | Fno. | 5.539 | 5.478 | 5.738 | 5.252 | 5.205 | 5.559 | 5.644 | 5.548 | 5.330 | 5.250 | 5.860 | 5.210 | 3.880 | 5.960 |
| ANGLE OF VIEW (DEG.) | 2ω | 192.2 | 195.7 | 191.8 | 194.4 | 195.7 | 193.8 | 211.2 | 209.6 | 223.3 | 226.4 | 214.9 | 226.9 | 223.3 | 214.0 |
| IMAGE HEIGHT | IH | 1.296 | 1.321 | 1.317 | 1.305 | 1.339 | 1.330 | 1.469 | 1.482 | 1.655 | 1.624 | 1.696 | 1.588 | 1.569 | 1.549 |
| FOCAL LENGTH OF FRONT GROUP | f_F | -1.169 | -1.025 | -1.356 | -0.907 | -0.834 | -0.902 | -0.943 | -0.808 | -0.988 | -0.927 | -0.777 | -1.018 | -0.743 | -0.767 |
| FOCAL LENGTH OF REAR GROUP | f_R | 1.672 | 1.689 | 1.814 | 1.487 | 1.728 | 1.647 | 1.681 | 1.848 | 1.998 | 1.890 | 2.122 | 1.904 | 1.793 | 1.931 |
| BACK FOCUS POSITION | Fb | 2.051 | 2.240 | 2.088 | 2.071 | 2.121 | 2.004 | 2.010 | 2.337 | 2.637 | 2.573 | 2.690 | 2.512 | 2.483 | 2.437 |
| RADIUS OF CURVATURE OF OBJECT-SIDE SURFACE OF SECOND LENS | r2a | -4.076 | -4.853 | -3.601 | -6.496 | -3.178 | -3.398 | -4.574 | -2.696 | -3.4470 | -2.9850 | -5.3310 | -2.0754 | -2.0555 | -4.1343 |
| ENTRANCE PUPIL POSITION AT MAXIMUM ANGLE OF VIEW | L_enp | 0.051 | 0.004 | 0.066 | 0.030 | 0.002 | 0.011 | -0.117 | -0.108 | -0.322 | -0.321 | 0.063 | -0.350 | -0.287 | 0.108 |
| ABBE NUMBER OF NEGATIVE LENS IN FOURTH LENS | νd | 18.90 | 18.90 | 18.90 | 17.77 | 17.77 | 17.77 | 17.77 | 17.77 | 18.90 | 18.90 | 18.90 | 17.77 | 17.77 | 18.90 |

FIG.2

| EXAMPLE NO. | | 1 | 2 | 3 | 4 | 5 | 6 | 7 | 8 | 9 | 10 | 11 | 12 | 13 | 14 | LOWER LIMIT | UPPER LIMIT |
|---|---|---|---|---|---|---|---|---|---|---|---|---|---|---|---|---|---|
| 1 | f_F/f_R | -0.699 | -0.607 | -0.748 | -0.610 | -0.483 | -0.548 | -0.561 | -0.437 | -0.494 | -0.490 | -0.366 | -0.535 | -0.414 | -0.397 | -0.800 | -0.300 |
| 2 | f_F/FL | -1.169 | -1.025 | -1.356 | -0.907 | -0.834 | -0.902 | -0.943 | -0.808 | -0.988 | -0.927 | -0.777 | -1.018 | -0.743 | -0.767 | -1.500 | -0.500 |
| 3 | Fb/FL | 2.051 | 2.240 | 2.088 | 2.071 | 2.121 | 2.004 | 2.010 | 2.337 | 2.637 | 2.573 | 2.690 | 2.512 | 2.483 | 2.437 | 1.700 | 3.500 |
| 4 | r2a/FL | -4.076 | -4.853 | -3.601 | -6.496 | -3.178 | -3.398 | -4.574 | -2.696 | -3.447 | -2.985 | -5.331 | -2.075 | -2.056 | -4.134 | -10.0 | -2.500 |
| 5 | L_enp/FL | 0.051 | 0.004 | 0.066 | 0.030 | 0.002 | 0.011 | -0.117 | -0.108 | -0.322 | -0.321 | 0.063 | -0.350 | -0.287 | 0.108 | -0.500 | 0.300 |
| 6 | νd | 18.90 | 18.90 | 18.90 | 17.77 | 17.77 | 17.77 | 17.77 | 17.77 | 18.90 | 18.90 | 18.90 | 17.77 | 17.77 | 18.90 | - | 20.00 | g 435.83 ---------
F 486.13 —·—·—
C 656.27 ············
d 587.56 ——————— g 435.83 - - - - - -
F 486.13 — · — · —
C 656.27 - - - - - - -
d 587.56 ——— g 435.83 - - - - - -
F 486.13 —·—·—
C 656.27 ············
d 587.56 ———

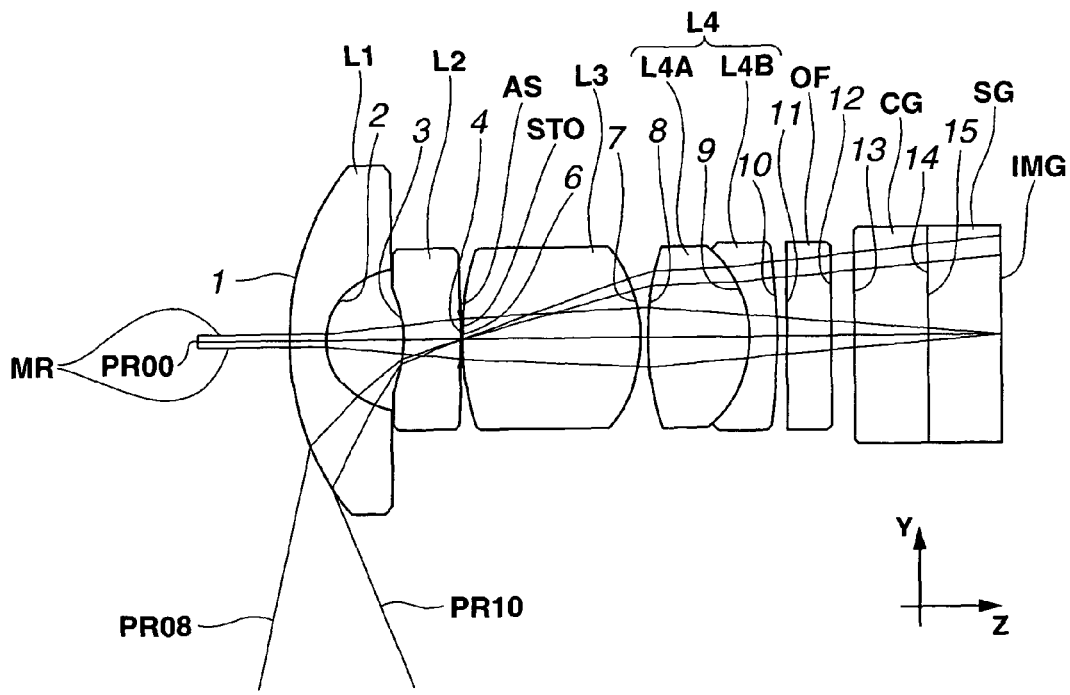
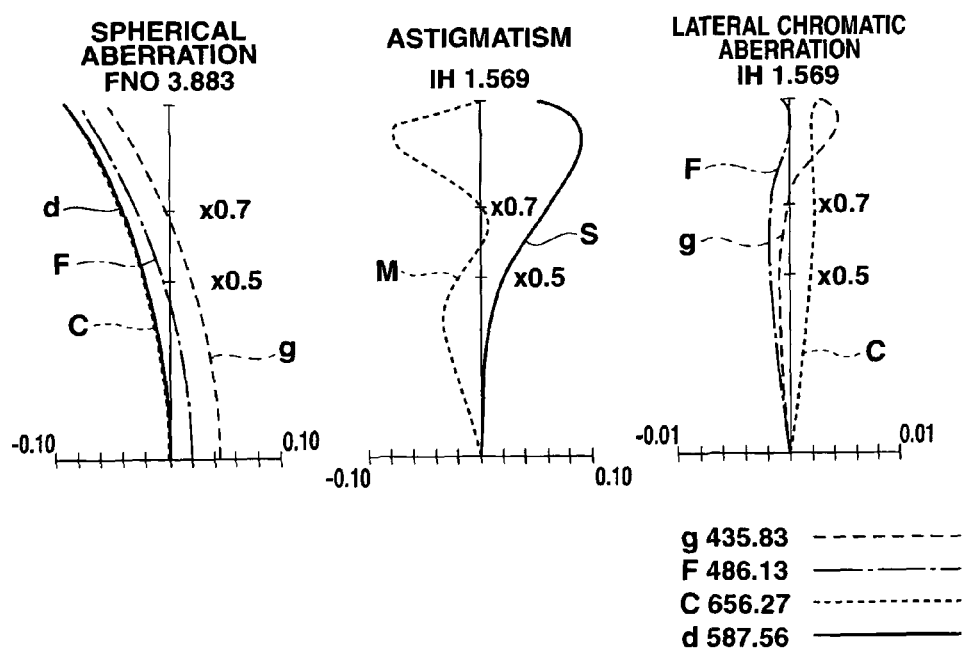

OBJECTIVE LENS AND ENDOSCOPE APPARATUS

CROSS REFERENCE TO RELATED APPLICATION

This application is a continuation application of PCT/JP2010/070482 filed on Nov. 17, 2010 and claims benefit of Japanese Applications No. 2009-277845 filed in Japan on Dec. 7, 2009, and No. 2010-205897 filed in Japan on Sep. 14, 2010, the entire contents of each of which are incorporated herein by their reference.

BACKGROUND OF THE INVENTION

1. Field of the Invention

The present invention relates to a small, wide-angle objective lens and an endoscope apparatus equipped with the objective lens.

2. Description of the Related Art

Since endoscopes are used to conduct observations, for example, in body cavities, there is need for small wide-angle objective lenses for endoscopes. Many of objective lenses for endoscopes proposed conventionally are those with an angle of view (2ω) of about 90° to 140°. For example, Japanese Patent Application Laid-Open Publication No. 10-20189 proposes an objective lens with an angle of view of 112° to 140°. Regarding wider-angle objective lenses, for example, Japanese Patent Application Laid-Open Publication No. 2006-251272 proposes an objective lens with an angle of view of 150° to 170°.

On the other hand, wide-angle objective lenses used in fields other than the endoscope field include, for example, an objective lens described in Japanese Utility Model Registration No. 3140304. The objective lens described in Japanese Utility-Model Registration No. 3140304 is an objective lens for an automotive recording apparatus and has an angle of view of 110° to 175°. Other examples of the wide-angle objective lenses used in fields other than the endoscope field include, for example, objective lenses described in Japanese Patent Application Laid-Open Publication No. 2004-258515 and Japanese Patent Application Laid-Open Publication No. 2004-29282. The objective lens described in the former one, i.e., in Japanese Patent Application Laid-Open Publication No. 2004-258515 is a fish-eye lens for a digital single-lens reflex camera with an angle of view of 180°. The objective lens described in the latter one, i.e., in Japanese Patent Application Laid-Open Publication No. 2004-29282 is a wide-angle lens for a surveillance camera with an angle of view of 128° to 139°.

Furthermore, examples of simple-structured lenses used in fields other than the endoscope field include a lens described in Japanese Patent Application Laid-Open Publication No. 9-297264. The lens described in Japanese Patent Application Laid-Open Publication No. 9-297264 is intended for use in a digital camera and has an angle of view of about 60°.

Recently, there has been demand for a still wider-angle objective lens for use in endoscopes. A reason for the demand for wider angles is related to reduction of inspection time. For example, when observing an object, such as the large intestine, which is a lumen containing folds therein, a user needs to bend a distal end of the endoscope to observe the back side of the folds. In so doing, an objective lens with a wide angle of view makes it possible to observe a large area at once, eliminating the need to bend the distal end of the endoscope or requiring only a small amount of bending, and thereby contributing to reduction of inspection time.

The objective lens according to example 3 of Japanese Utility Model Registration No. 3140304 described above has an angle of view of 175°, which is wider than the angle of view of the objective lens described in Japanese Patent Application Laid-Open Publication No. 10-20189. However, there is demand for a still wider angle for use in endoscopes.

SUMMARY OF THE INVENTION

According to one aspect of the present invention, there is provided an objective lens comprising, in order from an object side, a front group having negative refractive power, an aperture stop, and a rear group having positive refractive power, wherein: the front group comprises, in order from the object side, a first lens which is a negative meniscus lens with a convex surface turned to the object side and a second lens which is a negative lens with a concave surface turned to the object side; the rear group comprises, in order from the object side, a positive third lens and a fourth lens made up of a positive lens and a negative lens cemented together; and the objective lens satisfies conditional expression (1) below:

$$-0.8 < f\_F/f\_R < -0.3 \quad (1)$$

where $f\_F$ is a focal length of the front group, and $f\_R$ is a focal length of the rear group.

According to another aspect of the present invention, there is provided an endoscope apparatus comprising: the objective lens; and an observation screen configured to display an image formed by the objective lens, wherein an index configured to identify an angle of view is displayed on the observation screen.

BRIEF DESCRIPTION OF THE DRAWINGS

FIG. 1 is a chart showing specifications of objective lenses according to examples 1 to 14 of an embodiment of the present invention and element values of conditional expressions for the objective lenses;

FIG. 2 is a chart showing values of conditional expressions for the objective lenses according to examples 1 to 14 of the embodiment together with upper limit values and/or lower limit values assigned to the conditional expressions;

FIG. 31 is a drawing showing a configuration along an optical path of an optical system including the objective lens according to example 13 of the embodiment;

FIG. 32 is a drawing showing spherical aberration, astigmatism, and lateral chromatic aberration of the objective lens according to example 13 of the embodiment;

DETAILED DESCRIPTION OF THE PREFERRED EMBODIMENT

Figure 3:
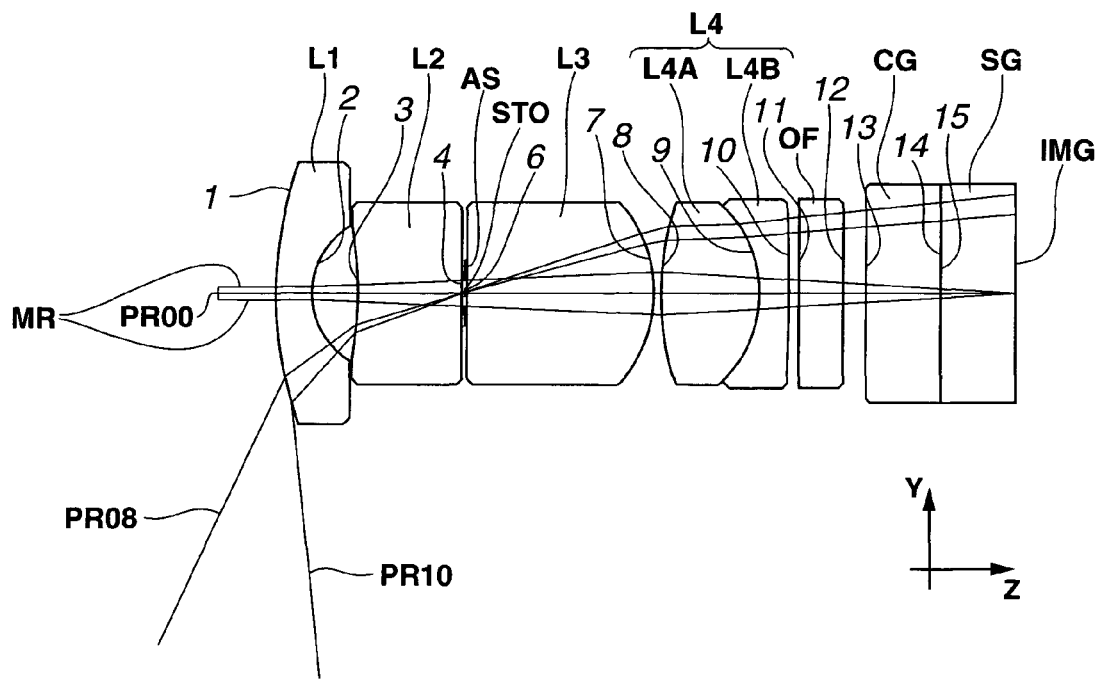
FIG. 3 is a drawing showing a configuration along an optical path of an optical system including the objective lens according to example 1 of the embodiment.

An embodiment of the present invention will be described below with reference to the drawings.

Embodiment

To begin with, symbols used in the present embodiment are as follows.
FL: Focal length of entire system
Fno.: F-number
2ω: Angle of view (in units of deg.)
IH: Image height
f_F: Focal length of front group
f_R: Focal length of rear group
Fb: Back focus position (distance from that surface of the fourth lens which is closest to an image side to a back focal point)
r2a: Radius of curvature of object-side surface of second lens
L_enp: Entrance pupil position at maximum angle of view (distance from a first surface, where a direction toward the image side corresponds to a positive direction)
νd: Abbe number of negative lens in fourth lens Next, the objective lens according to the embodiment of the present invention will be described.

A lens configuration of an optical system is important in order to realize a small, wide-angle objective lens with an angle of view of 180° or above. If it is necessary to simply achieve a wider angle, a configuration for gradually collecting off-axis light can be created by arranging a large number of lenses. However, such a configuration will increase total length of the optical system and outside diameter of a distal end of the objective lens, making it impossible to achieve downsizing. Thus, in order to achieve both wider angle and smaller size, it is desirable to use a configuration with a minimum necessary number of lenses.

Thus, the objective lens according to the present embodiment uses a basic configuration in which a front group with negative refractive power is placed on the object side of an aperture stop and a rear group with positive refractive power is placed on the image side of the aperture stop. The front group mainly acts to guide rays with a wide angle of view to the aperture stop and secure back focus of an entire lens system. The rear group mainly acts to form an image.

Regarding a configuration of the front group, a first lens is shaped as a negative meniscus with a convex surface turned to the object side, and is configured to collect principal off-axis rays with an angle of view of 180° or above and lead the collected off-axis rays to a second lens. The reason why the convex surface of the first lens is turned to the object side is that otherwise the principal off-axis rays with an angle of view of 180° or above cannot be collected.

The second lens is a negative lens with a concave surface turned to the object side. The geometry with the concave surface turned to the object side is unsuitable for collecting principal off-axis rays having a wide angle of view, but suitable for keeping down off-axis ray height. That is, since the first lens is configured to fully collect the principal off-axis rays with an angle of view of 180° or above, the second lens can be configured to keep down the off-axis ray height. The off-axis ray height is kept down as the second lens projects an image of the aperture stop to the vicinity of the second lens.

The rear group includes a positive third lens which mainly has image-forming effects and a fourth lens which mainly has chromatic aberration correction effects. The use of a cemented lens made up of a positive lens and a negative lens for the fourth lens located away from the aperture stop makes it possible to correct lateral chromatic aberration simultaneously with axial chromatic aberration.

With the above configuration set up, the objective lens according to the present embodiment further needs to satisfy conditional expression (1) below:

$$-0.8 < f\_F/f\_R < -0.3 \quad (1)$$

Conditional expression (1) is related to securing the angle of view and back focus and stipulates allotment of refractive power between the front group and the rear group. That is, when the ratio $f\_F/f\_R$ of the focal length $f\_F$ of the front group to the focal length $f\_R$ of the rear group is equal to or below a lower limit value of −0.8, it becomes difficult to secure the angle of view and back focus. For example, if the back focus is insufficient, optical members such a filter and cover glass cannot be placed between the fourth lens and an image plane. On the other hand, a value of $f\_F/f\_R$ equal to or above an upper limit value of −0.3 is advantageous in securing the angle of view and back focus, but undesirable for downsizing because of increased lens diameter of the rear group resulting from increases in the height of rays passing through the rear group. Thus, conditional expression (1) provides conditions for downsizing the rear group while securing the angle of view and back focus.

Preferably, the objective lens according to the present embodiment satisfies conditional expressions (2) and (3) below in addition to conditional expression (1).

$$-1.5 < f\_F/FL < -0.5 \quad (2)$$

$$1.7 < Fb/FL < 3.5 \quad (3)$$

Conditional expression (2) is related to lens outside diameter of the front group and stipulates the refractive power of the front group. When the ratio $f\_F/FL$ of the focal length $f\_F$ of the front group to the focal length FL of the entire system is equal to or below a lower limit value of −1.5, it becomes difficult to keep down the height of the off-axis rays passing through the front group, making it impossible to realize downsizing. On the other hand, a value of $f\_F/FL$ equal to or above an upper limit value of −0.5 is advantageous in keeping down the height of the off-axis rays passing through the front group, but makes it difficult to correct aberrations. That is, a value of $f\_F/FL$ equal to or above the upper limit value of −0.5 is undesirable because the Petzval sum takes a negative value, causing the image plane to incline toward a positive side.

Conditional expression (3) is related to the back focus described in conditional expression (1) and directly stipulates an appropriate range of back focus. When the ratio Fb/FL of the focal length Fb of the rear group to the focal length FL of the entire system is equal to or below a lower limit value of 1.7, the back focus becomes insufficient, which is disadvantageous in placing optical members such as a filter and cover glass. On the other hand, when Fb/FL is equal to or above an upper limit value of 3.5, the back focus becomes excessive, which is undesirable because the total length increases unnecessarily.

More preferably, the objective lens according to the present embodiment satisfies conditional expressions (4) to (6) below in addition to conditional expressions (1) to (3).

$$-10 < r2a/FL < -2.5 \quad (4)$$

$$-0.5 < L\_enp/FL < 0.3 \quad (5)$$

$$vd < 20 \quad (6)$$

Among conditional expressions (4) to (6), conditional expressions (4) and (5) are related to downsizing of the front group. Conditional expression (4) stipulates an object-side surface shape of the second lens. If the ratio $r2a/FL$ of radius of curvature r2a of the object-side surface of the second lens to the focal length FL of the entire system is equal to or below a lower limit value of −10, it becomes difficult to keep down the height of the off-axis rays passing through the front group. On the other hand, when r2a/FL is equal to or above an upper limit value of −2.5, the radius of curvature r2a of the object-side surface of the second lens is decreased, which is undesirable because the off-axis rays become prone total reflection.

Conditional expression (5) stipulates entrance pupil position at a maximum angle of view. Desirably, the entrance pupil position at the maximum angle of view is located near the first lens. If the ratio $L\_enp/FL$ of the entrance pupil position L_enp at the maximum angle of view to the focal length FL of the entire system is equal to or above an upper limit value of 0.3, the off-axis rays passing through the front group tend to increase in height. On the other hand, when L_enp/FL is equal to or below a lower limit value of −0.5, convex shape on the object side of the first lens is enhanced. Consequently, that surface of the objective lens which is closest to the object side increases in an amount of protrusion when the objective lens is placed in distal end part of an endoscope. This is undesirable because a distal end portion of the lens becomes vulnerable to damage.

Conditional expression (6) is related to chromatic aberration correction and stipulates the Abbe number vd of the negative lens in the fourth lens. Correction of lateral chromatic aberration is particularly important for an objective lens with a large angle of view and with a lens configuration in which a front group with negative refractive power and a rear group with positive refractive power are placed on both sides of an aperture stop, as in the case of the objective lens according to the present embodiment. Thus, it is advisable that a cemented lens is used for the fourth lens located away from the aperture stop and that the negative lens in the fourth lens has an Abbe number of less than 20.

Examples of glass material with an Abbe number of less than 20 include the following:
(Example 1 of Glass Material)
Glass material name: S-NPH2
Abbe number (vd): 18.90
Glass code: 923189
OHARA INC.
(Example 2 of Glass Material)
Glass material name: K-PSFn214
Abbe number (vd): 17.77
Glass code: 144178
SUMITA OPTICAL GLASS, Inc.

Both examples 1 and 2 of glass material have large chromatic dispersion and extremely high chromatic aberration correction capacity. The use of such glass material for the negative lens in the fourth lens makes it possible to correct lateral chromatic aberration effectively. Incidentally, glass material other than examples 1 and 2 of glass material described above also provides similar chromatic aberration correction effects as long as the glass material has an Abbe number (νd) of less than 20.

Furthermore, preferably the objective lens according to the present embodiment is an endoscope objective lens applied to an endoscope as described above, and has an angle of view (2ω) of 180° or above. The use of an endoscope objective lens with an angle of view (2ω) of more than 180° makes it possible to observe an area covered by a wider angle than before.

Also, a field lens may be placed near an image-forming plane of the objective lens according to the present embodiment. The field lens is intended to convert exit pupil position. The field lens, if installed, makes it possible to control an angle of rays incident on an image pickup device, and in particular, perform proper angle control around the perimeter of a screen. Whether to give positive refractive power or negative refractive power to the field lens may be determined appropriately as required.

Preferably, the fourth lens of the objective lens according to the present embodiment is made up of a positive lens and a negative lens placed and cemented together in this order from the object side because of the capability to properly correct lateral chromatic aberration. However, the fourth lens may be made up of a negative lens and a positive lens placed and cemented together in this order from the object side.

Next, examples 1 to 14 of the objective lens according to the present embodiment will be described with reference to FIGS. 1 to 37.

FIG. 1 is a chart showing specifications of objective lenses according to examples 1 to 14 and element values of the above-described conditional expressions.

FIG. 2 is a chart showing values of conditional expressions for the objective lenses according to examples 1 to 14 together with upper limit values and/or lower limit values assigned to the conditional expressions. As can be seen from the chart, the objective lenses according to examples 1 to 11 and 14 satisfy conditional expressions (1) to (6) described above. The objective lenses according to examples 12 and 13 satisfy conditional expressions (1) to (6) excluding conditional expression (4).

Configurations along an optical path of an optical system including the objective lenses according to examples 1 to 14 are shown in FIGS. 3, 5, 7, 9, 11, 13, 15, 17, 19, 22, 25, 28, 31, and 34, respectively. In these figures, a direction of an optical axis of the optical system is designated as a z direction and a direction of image height is designated as a y direction. Also, aberration diagrams of the objective lenses according to examples 1 to 14 are shown in FIGS. 4, 6, 8, 10, 12, 14, 16, 18, 20, 23, 26, 29, 32, and 35, respectively. Furthermore, aspherical shapes of image-side surfaces (surface No. 2 as described below) of the first lenses of the objective lenses according to examples 9 to 13 are shown as S2 in FIGS. 21, 24, 27, 30, and 33, respectively.

In the configuration diagrams along the optical path of the optical system including the objective lens, reference character L1 denotes the first lens; reference character L2 denotes the second lens; reference character AS denotes the aperture stop; reference character L3 denotes the third lens; reference character L4 denotes the fourth lens (the positive lens on the object side of the fourth lens L4 is denoted by reference character L4A and the negative lens on the image side of the fourth lens L4 is denoted by reference character L4B); reference character OF denotes an optical member which is assumed to be an optical filter such as a laser cut filter, an infrared cut filter, or an optical low-pass filter; reference character CG denotes CCD cover glass, and reference character SG denotes CCD chip sealing glass. Also, the direction of the optical axis is designated as the Z direction and the direction of height from the optical axis is designated as the Y direction. Furthermore, reference character PR00 denotes the optical axis, reference character MR denotes an axial marginal ray, reference character PR08 denotes a principal ray at an image height ratio of 0.8, and reference character PR10 denotes a principal ray at an image height ratio of 1.

In examples 1 to 5 and 8 to 14, surface numbers of optical surfaces are as follows: the object side of the first lens L1 is assigned 1, the image side of the first lens L1 is assigned 2, the object side of the second lens L2 is assigned 3, the image side of the second lens L2 is assigned 4, the aperture stop AS is assigned STO ("STO" is used here instead of the surface number of "5"), the object side of the third lens L3 is assigned 6, the image side of the third lens L3 is assigned 7, the object side of the positive lens L4A on the object side of the fourth lens L4 is assigned 8, a cemented surface between the positive lens L4A on the object side and negative lens L4B on the image side of the fourth lens L4 is assigned 9, the image side of the negative lens L4B on the image side of the fourth lens L4 is assigned 10, the object side of the optical member OF is assigned 11, the image side of the optical member OF is assigned 12, the object side of the CCD cover glass CG is assigned 13, the image side of the CCD cover glass CG is assigned 14, and the object side of the CCD chip sealing glass SG is assigned 15. The image plane IMG is located on the object side of the CCD chip sealing glass SG.

Examples 6 and 7 differ from the other examples in arrangement of optical members. Specifically, two optical members—a first optical member OF1 and a second optical member OF2—are provided, and placed between the second lens L2 and the aperture stop AS. Therefore, although the surface numbers of the optical surfaces up to the second lens L2 are the same as in examples 1 to 5 and 8 to 14, the surface numbers of the optical surfaces closer to the image side are as follows: the object side of the first optical member OF1 is assigned 5, the image side of the first optical member OF1 is assigned 6, the object side of the second optical member OF2 is assigned 7, the image side of the second optical member OF2 is assigned 8, the aperture stop AS is assigned STO, the object side of the third lens L3 is assigned 10, the image side of the third lens L3 is assigned 11, the object side of the positive lens L4A on the object side of the fourth lens L4 is assigned 12, the cemented surface between the positive lens L4A on the object side and negative lens L4B on the image side of the fourth lens L4 is assigned 13, the image side of the negative lens L4B on the image side of the fourth lens L4 is assigned 14, the object side of the CCD cover glass CG is assigned 15, the image side of the CCD cover glass CG is assigned 16, and the object side of the CCD chip sealing glass SG is assigned 17. The image plane IMG is located on the object side of the CCD chip sealing glass SG, similarly to the above examples.

Furthermore, each aberration diagram shows a g line (with a wavelength of 435.83 nm), an F line (with a wavelength of 486.13 nm), a C line (with a wavelength of 656.27 nm), a d line (with a wavelength of 587.56 nm), a meridional line M, and a sagittal line S.

In addition, in the numeric data of the examples shown below, "INF" represents infinity and a symbol $ is attached to the surface numbers of aspherical surfaces (ASP). The refractive index is a value for the d line (i.e., at a wavelength of 587.56 nm). OBJ denotes an object plane while IMG denotes the image plane as described above. In the numeric data of the aspherical surfaces, symbol "RDY" denotes a paraxial radius of curvature, symbol "K" denotes a conic constant, symbols "AC2" to "AC10" denote second to tenth even order aspherical constants in the aspherical equation shown below, and symbol "E" and a subsequent numeral denote the power of 10. (Aspherical Equation)

$$Z = \frac{\left(\frac{1}{RDY}\right) \times Y^2}{1 + \sqrt{1 - (K+1) \times \left(\frac{1}{RDY}\right)^2 \times Y^2}} + AC2 \times Y^2 + AC4 \times Y^4 + AC6 \times Y^6 + AC8 \times Y^8 + AC10 \times Y^{10}$$ [Formula 1]

In the aspherical equation, again Y denotes the height from the optical axis and Z denotes a coordinate of the aspherical surface in the direction of the optical axis. However, only in the aspherical equation, the origin of the Z-axis is set at a position where Y=0.

EXAMPLE 1

Figure 4:
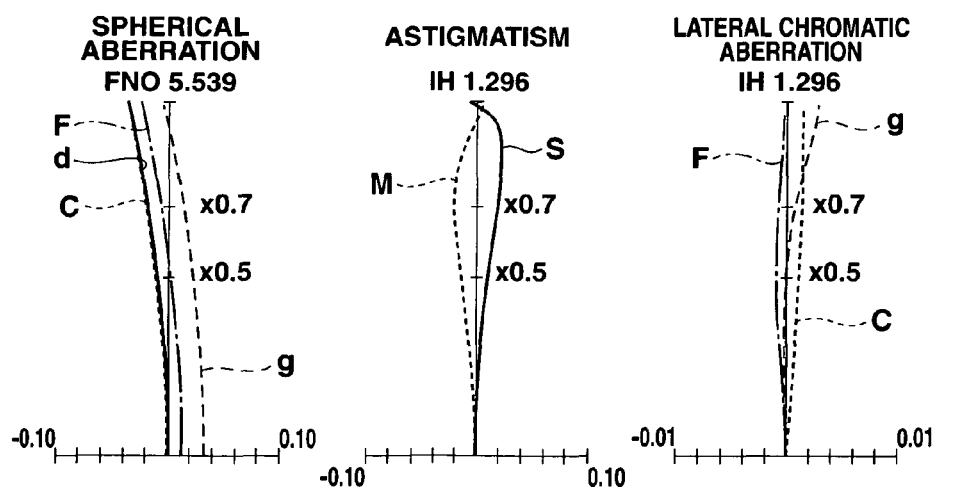
FIG. 4 is a drawing showing spherical aberration, astigmatism, and lateral chromatic aberration of the objective lens according to example 1 of the embodiment.

FIG. 3 is a drawing showing a configuration along the optical path of the optical system including the objective lens according to example 1 and FIG. 4 is a drawing showing spherical aberration, astigmatism, and lateral chromatic aberration of the objective lens according to example 1.

As shown in FIG. 3, the objective lens according to example 1 includes, in order from the object side, a first lens L1 which is a negative meniscus lens with a convex surface turned to the object side, a second lens L2 which is a negative meniscus lens with a concave surface turned to the object side, an aperture stop AS, a third lens L3 which is a plano-convex lens (positive lens) with a convex surface turned to the image side, and a fourth lens L4 which is a cemented lens made up of a positive, double-convex lens L4A and a negative meniscus lens L4B with a concave surface turned to the object side. The negative lens L4B in the fourth lens L4 is made of glass material S-NPH2 with an Abbe number (vd) of 18.90. The lenses L1 and L2 make up a front group with negative refractive power while lenses L3 and L4 make up a rear group with positive refractive power.

On the image side of the fourth lens L4, the above-described optical member OF, CCD cover glass CG, and CCD chip sealing glass SG are placed in order from the object side.

FIG. 3 shows rays including an axial marginal ray MR, a principal ray PR10 forming an image at a maximum angle of view of 192.2° at an image height ratio of 1 (an image height of 1.296), and a principal ray PR08 forming an image at an image height ratio of 0.8 (an image height of 1.296×0.8) as well as an optical axis PR00.

The spherical aberration, astigmatism, and lateral chromatic aberration are as shown in FIG. 4.

Numeric data of the optical system according to example 1 is shown below.

TABLE 1

| Surface number | Radius of curvature | Spacing | Refractive index | Abbe number vd |
|---|---|---|---|---|
| OBJ | INF | INF | 1. | |
| 1 | 5.1465 | 0.4812 | 1.88300 | 40.76 |
| 2 | 1.0567 | 0.5919 | 1. | |

TABLE 1-continued

| Surface number | Radius of curvature | Spacing | Refractive index | Abbe number vd |
|---|---|---|---|---|
| 3 | −4.0762 | 1.3950 | 1.88300 | 40.76 |
| 4 | −29.7830 | 0.0192 | 1. | |
| STO | INF | 0.0290 | 1. | |
| 6 | INF | 2.4069 | 1.88300 | 40.76 |
| 7 | −1.9029 | 0.0962 | 1. | |
| 8 | 4.0188 | 1.2696 | 1.72916 | 54.68 |
| 9 | −1.6134 | 0.3850 | 1.92286 | 18.90 |
| 10 | −17.7120 | 0.1251 | 1. | |
| 11 | INF | 0.5775 | 1.51800 | 75.00 |
| 12 | INF | 0.3068 | 1. | |
| 13 | INF | 0.9625 | 1.51633 | 64.14 |
| 14 | INF | 0.0096 | 1.51000 | 64.10 |
| 15 | INF | 0.9625 | 1.61061 | 50.20 |
| IMG | INF | 0. | | |

EXAMPLE 2

Figure 5:
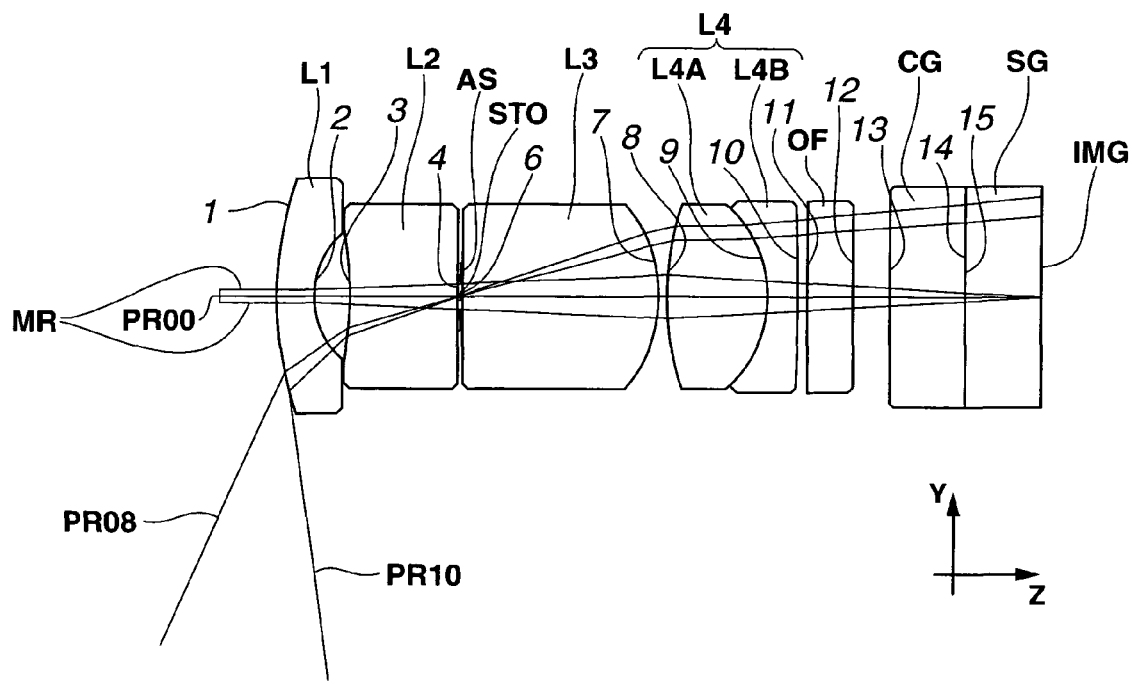
FIG. 5 is a drawing showing a configuration along an optical path of an optical system including the objective lens according to example 2 of the embodiment.
Figure 6:
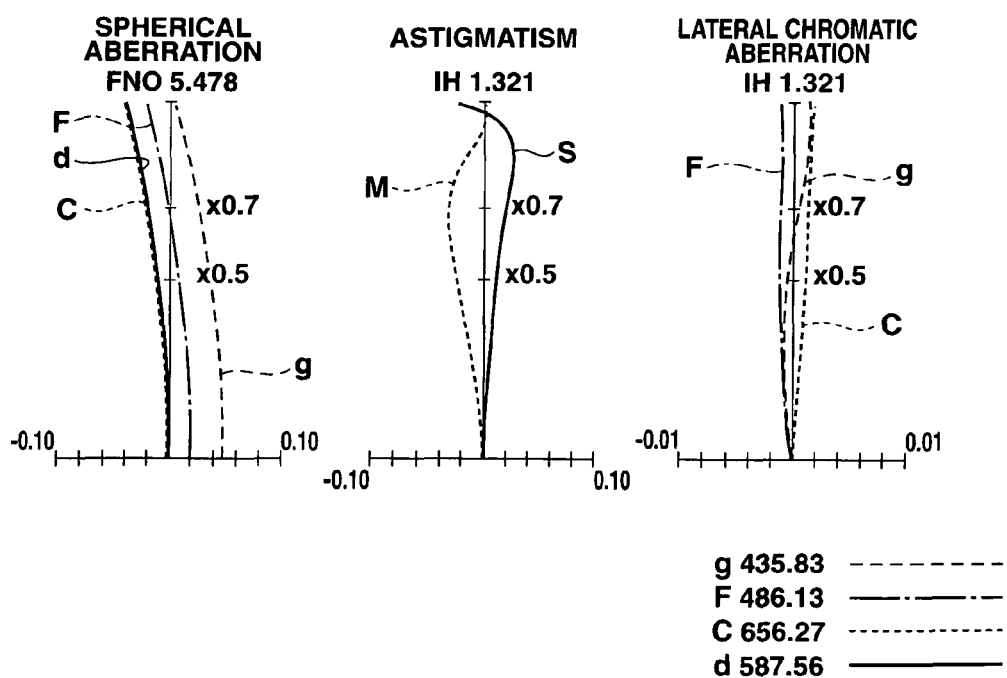
FIG. 6 is a drawing showing spherical aberration, astigmatism, and lateral chromatic aberration of the objective lens according to example 2 of the embodiment.

FIG. 5 is a drawing showing a configuration along the optical path of the optical system including the objective lens according to example 2 and FIG. 6 is a drawing showing spherical aberration, astigmatism, and lateral chromatic aberration of the objective lens according to example 2.

As shown in FIG. 5, the objective lens according to example 2 includes, in order from the object side, a first lens L1 which is a negative meniscus lens with a convex surface turned to the object side, a second lens L2 which is a plano-concave lens (negative lens) with a concave surface turned to the object side, an aperture stop AS, a third lens L3 which is a plano-convex lens (positive lens) with a convex surface turned to the image side, and a fourth lens L4 which is a cemented lens made up of a positive, double-convex lens L4A and a negative meniscus lens L4B with a concave surface turned to the object side. The negative lens L4B in the fourth lens L4 is made of glass material S-NPH2 with an Abbe number (vd) of 18.90. The lenses L1 and L2 make up a front group with negative refractive power while lenses L3 and L4 make up a rear group with positive refractive power.

On the image side of the fourth lens L4, the above-described optical member OF, CCD cover glass CG, and CCD chip sealing glass SG are placed in order from the object side.

FIG. 5 shows rays including an axial marginal ray MR, a principal ray PR10 forming an image at a maximum angle of view of 195.7° at an image height ratio of 1 (an image height of 1.321), and a principal ray PR08 forming an image at an image height ratio of 0.8 (an image height of 1.321×0.8) as well as an optical axis PR00.

The spherical aberration, astigmatism, and lateral chromatic aberration are as shown in FIG. 6.

Numeric data of the optical system according to example 2 is shown below.

TABLE 2

| Surface number | Radius of curvature | Spacing | Refractive index | Abbe number vd |
|---|---|---|---|---|
| OBJ | INF | INF | 1. | |
| 1 | 4.4620 | 0.4909 | 2.17840 | 33.00 |
| 2 | 1.1005 | 0.4557 | 1. | |
| 3 | −4.8533 | 1.4304 | 1.88300 | 40.76 |
| 4 | INF | 0.0196 | 1. | |
| STO | INF | 0.0295 | 1. | |
| 6 | INF | 2.5538 | 1.88300 | 40.76 |
| 7 | −1.9332 | 0.0982 | 1. | |
| 8 | 3.9915 | 1.3346 | 1.72916 | 54.68 |
| 9 | −1.6141 | 0.3927 | 1.92286 | 18.90 |

TABLE 2-continued

| Surface number | Radius of curvature | Spacing | Refractive index | Abbe number vd |
|---|---|---|---|---|
| 10 | −19.1193 | 0.1276 | 1. | |
| 11 | INF | 0.5891 | 1.51800 | 75.00 |
| 12 | INF | 0.4610 | 1. | |
| 13 | INF | 0.9818 | 1.51633 | 64.14 |
| 14 | INF | 0.0098 | 1.51000 | 64.10 |
| 15 | INF | 0.9818 | 1.61061 | 50.20 |
| IMG | INF | 0. | | |

EXAMPLE 3

Figure 7:
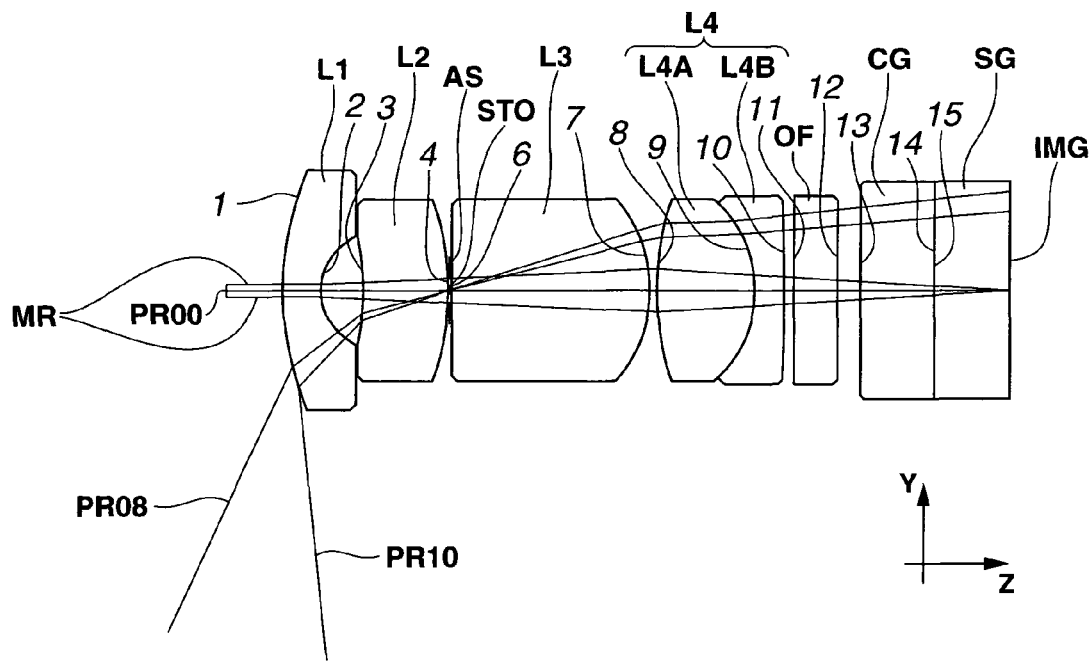
FIG. 7 is a drawing showing a configuration along an optical path of an optical system including the objective lens according to example 3 of the embodiment.
Figure 8:
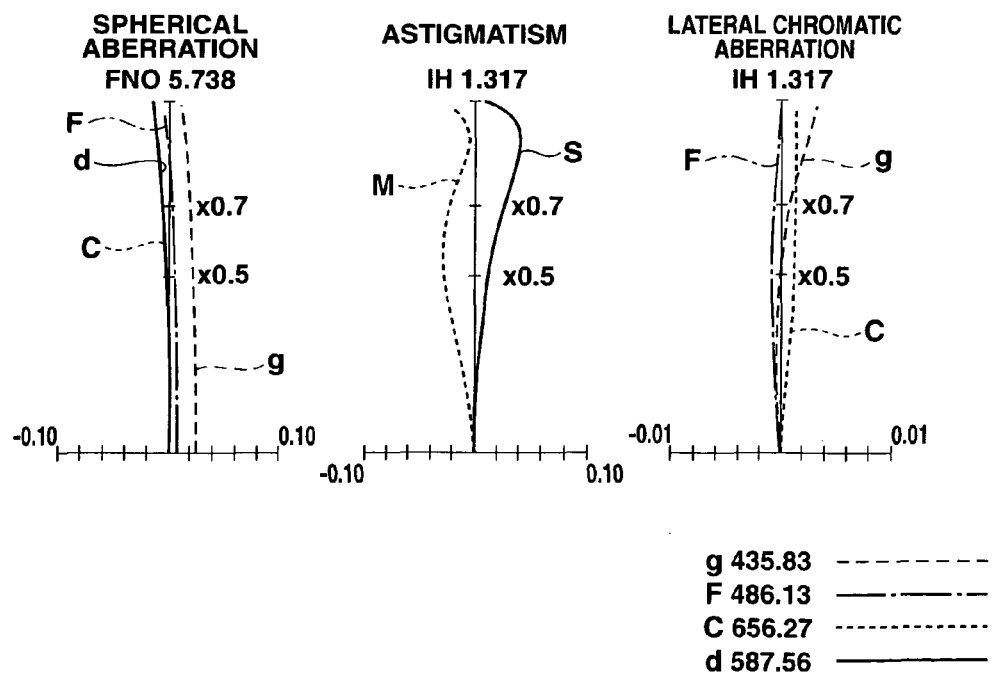
FIG. 8 is a drawing showing spherical aberration, astigmatism, and lateral chromatic aberration of the objective lens according to example 3 of the embodiment.

FIG. 7 is a drawing showing a configuration along the optical path of the optical system including the objective lens according to example 3 and FIG. 8 is a drawing showing spherical aberration, astigmatism, and lateral chromatic aberration of the objective lens according to example 3.

As shown in FIG. 7, the objective lens according to example 3 includes, in order from the object side, a first lens L1 which is a negative meniscus lens with a convex surface turned to the object side, a second lens L2 which is a negative meniscus lens with a concave surface turned to the object side, an aperture stop AS, a third lens L3 which is a plano-convex lens (positive lens) with a convex surface turned to the image side, and a fourth lens L4 which is a cemented lens made up of a positive, double-convex lens L4A and a negative meniscus lens L4B with a concave surface turned to the object side. Among these lenses, the first lens L1 has an aspherical surface on the image side and an aspherical shape of the image-side surface is configured such that the negative refractive power will decrease with distance from the optical axis. The negative lens L4B in the fourth lens L4 is made of glass material S-NPH2 with an Abbe number (vd) of 18.90. The lenses L1 and L2 make up a front group with negative refractive power while lenses L3 and L4 make up a rear group with positive refractive power.

On the image side of the fourth lens L4, the above-described optical member OF, CCD cover glass CG, and CCD chip sealing glass SG are placed in order from the object side.

FIG. 7 shows rays including an axial marginal ray MR, a principal ray PR10 forming an image at a maximum angle of view of 191.80° at an image height ratio of 1 (an image height of 1.317), and a principal ray PR08 forming an image at an image height ratio of 0.8 (an image height of 1.317×0.8) as well as an optical axis PR00.

The spherical aberration, astigmatism, and lateral chromatic aberration are as shown in FIG. 8.

Numeric data of the optical system according to example 3 is shown below.

TABLE 3

| Surface number | Radius of curvature | Spacing | Refractive index | Abbe number vd |
|---|---|---|---|---|
| OBJ | INF | INF | 1. | |
| 1 | 4.3298 | 0.4891 | 1.88300 | 40.76 |
| 2$ | 0.8108 | 0.5625 | 1. | |
| 3 | −3.6006 | 1.1202 | 1.88300 | 40.76 |
| 4 | −4.2697 | 0.0196 | 1. | |
| STO | INF | 0.0276 | 1. | |
| 6 | INF | 2.5704 | 1.88300 | 40.76 |
| 7 | −2.1856 | 0.0978 | 1. | |
| 8 | 3.9565 | 1.3123 | 1.72916 | 54.68 |
| 9 | −1.6309 | 0.3913 | 1.92286 | 18.90 |
| 10 | −11.9682 | 0.1272 | 1. | |
| 11 | INF | 0.5869 | 1.51800 | 75.00 |

TABLE 3-continued

| Surface number | Radius of curvature | Spacing | Refractive index | Abbe number vd |
|---|---|---|---|---|
| 12 | INF | 0.3157 | 1. | |
| 13 | INF | 0.9782 | 1.51633 | 64.14 |
| 14 | INF | 0.0098 | 1.51000 | 64.10 |
| 15 | INF | 0.9782 | 1.61061 | 50.20 |
| IMG | INF | 0. | | |
| S2 ASP | RDY | K | | |
| | 0.8108 | 0.1546 | | |
| AC2 | AC4 | AC6 | AC8 | AC10 |
| 0.0000E+00 | −4.2044E−02 | −3.0553E−02 | 0.0000E+00 | 0.0000E+00 |

EXAMPLE 4

Figure 9:
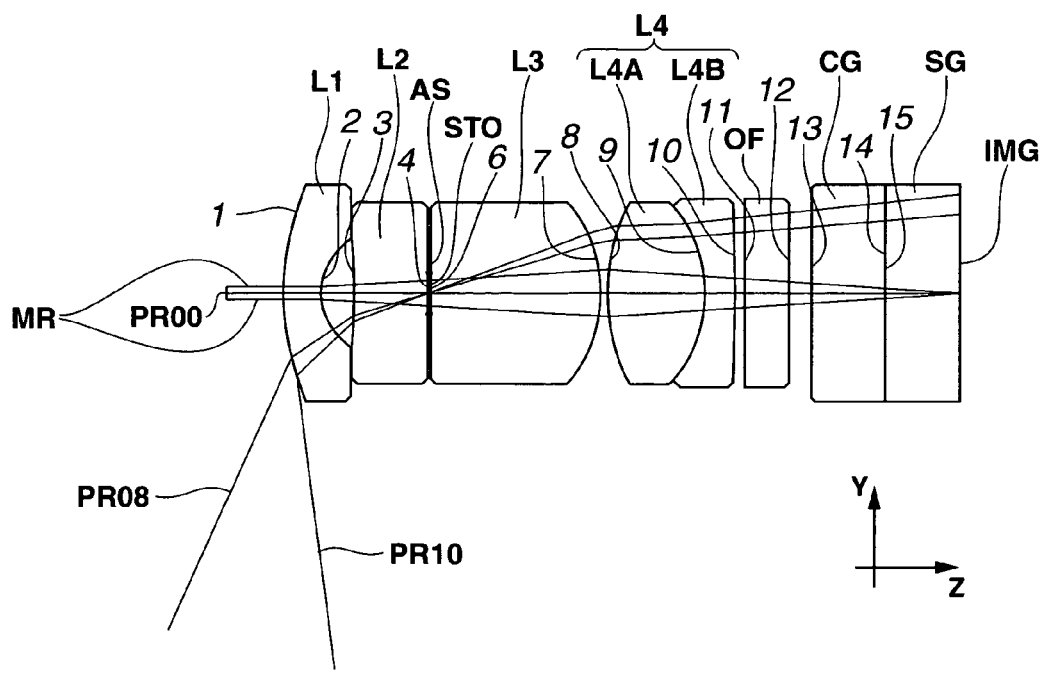
FIG. 9 is a drawing showing a configuration along an optical path of an optical system including the objective lens according to example 4 of the embodiment.
Figure 10:
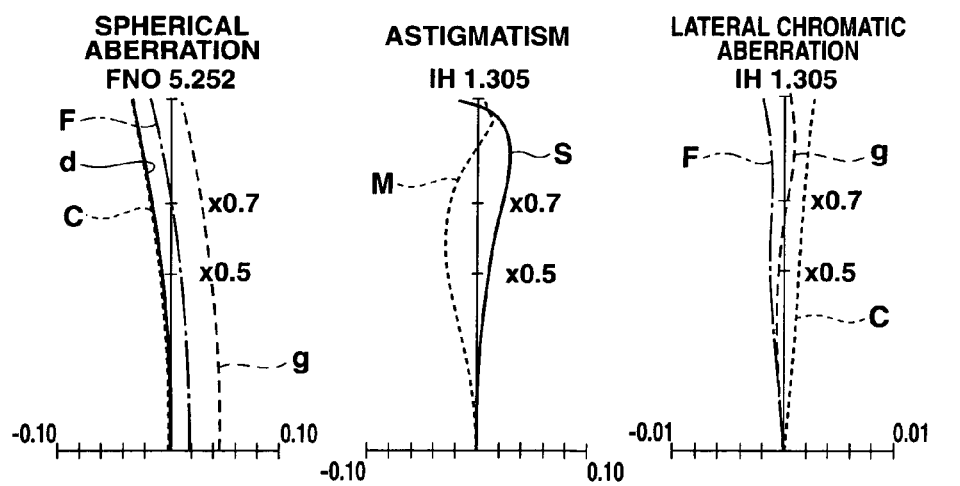
FIG. 10 is a drawing showing spherical aberration, astigmatism, and lateral chromatic aberration of the objective lens according to example 4 of the embodiment.

FIG. 9 is a drawing showing a configuration along the optical path of the optical system including the objective lens according to example 4 and FIG. 10 is a drawing showing spherical aberration, astigmatism, and lateral chromatic aberration of the objective lens according to example 4.

As shown in FIG. 9, the objective lens according to example 4 includes, in order from the object side, a first lens L1 which is a negative meniscus lens with a convex surface turned to the object side, a second lens L2 which is a plano-concave lens (negative lens) with a concave surface turned to the object side, an aperture stop AS, a third lens L3 which is a plano-convex lens (positive lens) with a convex surface turned to the image side, and a fourth lens L4 which is a cemented lens made up of a positive, double-convex lens L4A and a negative meniscus lens L4B with a concave surface turned to the object side. Among these lenses, the first lens L1 has an aspherical surface on the image side and an aspherical shape of the image-side surface is configured such that the negative refractive power will decrease with distance from the optical axis. The negative lens L4B in the fourth lens L4 is made of glass material K-PSFn214 with an Abbe number (vd) of 17.77. The lenses L1 and L2 make up a front group with negative refractive power while lenses L3 and L4 make up a rear group with positive refractive power.

On the image side of the fourth lens L4, the above-described optical member OF, CCD cover glass CG, and CCD chip sealing glass SG are placed in order from the object side.

FIG. 9 shows rays including an axial marginal ray MR, a principal ray PR10 forming an image at a maximum angle of view of 194.4° at an image height ratio of 1 (an image height of 1.305), and a principal ray PR08 forming an image at an image height ratio of 0.8 (an image height of 1.305×0.8) as well as an optical axis PR00.

The spherical aberration, astigmatism, and lateral chromatic aberration are as shown in FIG. 10.

Numeric data of the optical system according to example 4 is shown below.

TABLE 4

| Surface number | Radius of curvature | Spacing | Refractive index | Abbe number vd |
|---|---|---|---|---|
| OBJ | INF | INF | 1. | |
| 1 | 3.7076 | 0.4849 | 2.17840 | 33.00 |
| 2$ | 0.8833 | 0.4369 | 1. | |
| 3 | −6.4963 | 0.9812 | 1.88300 | 40.76 |
| 4 | INF | 0.0194 | 1. | |
| STO | INF | 0.0291 | 1. | |
| 6 | INF | 2.2415 | 1.88300 | 40.76 |
| 7 | −1.7530 | 0.0970 | 1. | |
| 8 | 2.8729 | 1.2611 | 1.72916 | 54.68 |
| 9 | −1.8226 | 0.3879 | 2.14352 | 17.77 |

TABLE 4-continued

| Surface number | Radius of curvature | Spacing | Refractive index | Abbe number vd |
|---|---|---|---|---|
| 10 | −16.5518 | 0.1261 | 1. | |
| 11 | INF | 0.5819 | 1.51800 | 75.00 |
| 12 | INF | 0.3133 | 1. | |
| 13 | INF | 0.9698 | 1.51633 | 64.14 |
| 14 | INF | 0.0097 | 1.51000 | 64.10 |
| 15 | INF | 0.9698 | 1.61061 | 50.20 |
| IMG | INF | 0. | | |
| S2 ASP | RDY 0.8833 | K 0.2076 | | |
| AC2 0.0000E+00 | AC4 −2.6023E−02 | AC6 −1.6619E−02 | AC8 0.0000E+00 | AC10 0.0000E+00 |

EXAMPLE 5

Figure 11:
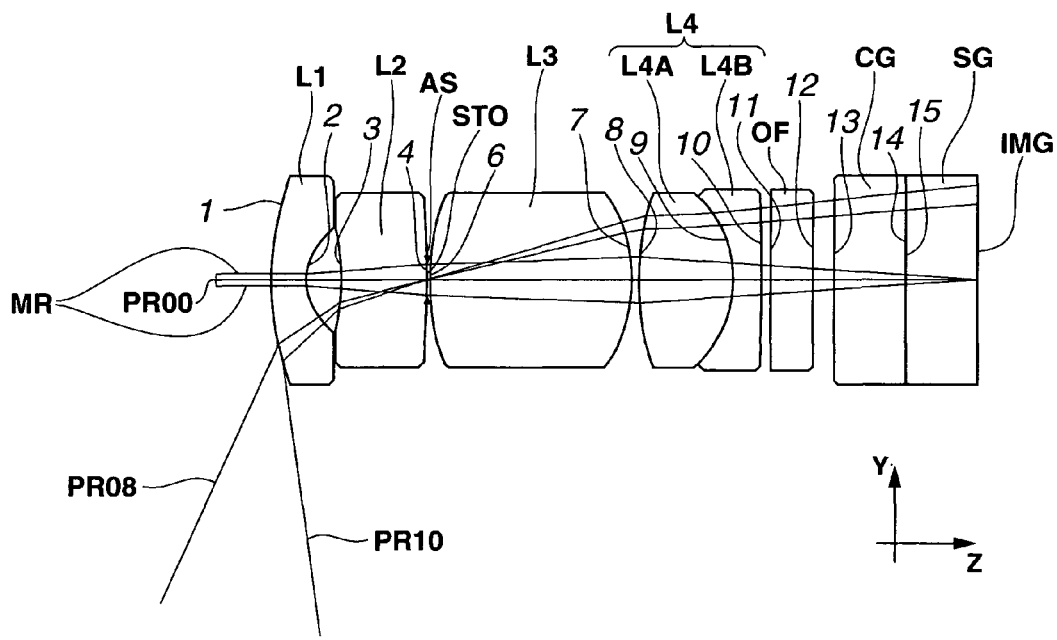
FIG. 11 is a drawing showing a configuration along an optical path of an optical system including the objective lens according to example 5 of the embodiment.
Figure 12:
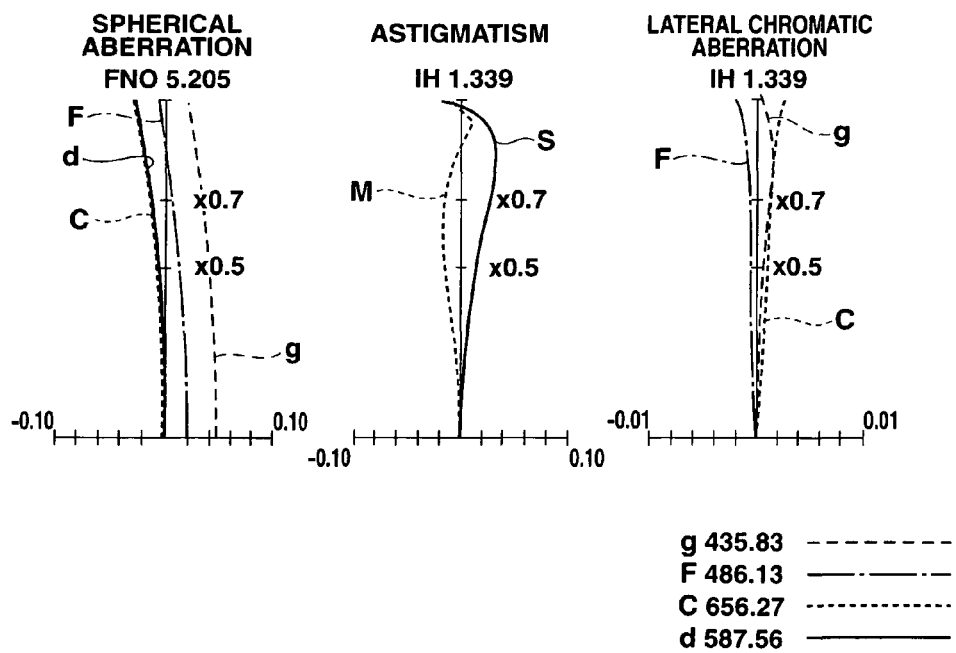
FIG. 12 is a drawing showing spherical aberration, astigmatism, and lateral chromatic aberration of the objective lens according to example 5 of the embodiment.

FIG. 11 is a drawing showing a configuration along the optical path of the optical system including the objective lens according to example 5 and FIG. 12 is a drawing showing spherical aberration, astigmatism, and lateral chromatic aberration of the objective lens according to example 5.

As shown in FIG. 11, the objective lens according to example 5 includes, in order from the object side, a first lens L1 which is a negative meniscus lens with a convex surface turned to the object side, a second lens L2 which is a negative meniscus lens with a concave surface turned to the object side, an aperture stop AS, a third lens L3 which is a double-convex lens (positive lens), and a fourth lens L4 which is a cemented lens made up of a positive, double-convex lens L4A and a negative meniscus lens L4B with a concave surface turned to the object side. The negative lens L4B in the fourth lens L4 is made of glass material K-PSFn214 with an Abbe number (vd) of 17.77. The lenses L1 and L2 make up a front group with negative refractive power while lenses L3 and L4 make up a rear group with positive refractive power.

On the image side of the fourth lens L4, the above-described optical member OF, CCD cover glass CG, and CCD chip sealing glass SG are placed in order from the object side.

FIG. 11 shows rays including an axial marginal ray MR, a principal ray PR10 forming an image at a maximum angle of view of 195.7° at an image height ratio of 1 (an image height of 1.339), and a principal ray PR08 forming an image at an image height ratio of 0.8 (an image height of 1.339×0.8) as well as an optical axis PR00.

The spherical aberration, astigmatism, and lateral chromatic aberration are as shown in FIG. 12.

Numeric data of the optical system according to example 5 is shown below.

TABLE 5

| Surface number | Radius of curvature | Spacing | Refractive index | Abbe number vd |
|---|---|---|---|---|
| OBJ | INF | INF | 1. | |
| 1 | 4.2090 | 0.4976 | 2.17840 | 33.00 |
| 2 | 0.9136 | 0.4904 | 1. | |
| 3 | −3.1778 | 1.2243 | 1.88300 | 40.76 |
| 4 | −17.2835 | 0.0199 | 1. | |
| STO | INF | 0.0299 | 1. | |
| 6 | 3.8124 | 2.7742 | 1.88300 | 40.76 |
| 7 | −2.3793 | 0.0995 | 1. | |
| 8 | 3.3845 | 1.3553 | 1.72916 | 54.68 |
| 9 | −1.6841 | 0.3981 | 2.14352 | 17.77 |
| 10 | −7.9766 | 0.1294 | 1. | |
| 11 | INF | 0.5971 | 1.51800 | 75.00 |
| 12 | INF | 0.3177 | 1. | |
| 13 | INF | 0.9951 | 1.51633 | 64.14 |

TABLE 5-continued

| Surface number | Radius of curvature | Spacing | Refractive index | Abbe number vd |
|---|---|---|---|---|
| 14 | INF | 0.0100 | 1.51000 | 64.10 |
| 15 | INF | 0.9951 | 1.61061 | 50.20 |
| IMG | INF | 0. | | |

EXAMPLE 6

Figure 13:
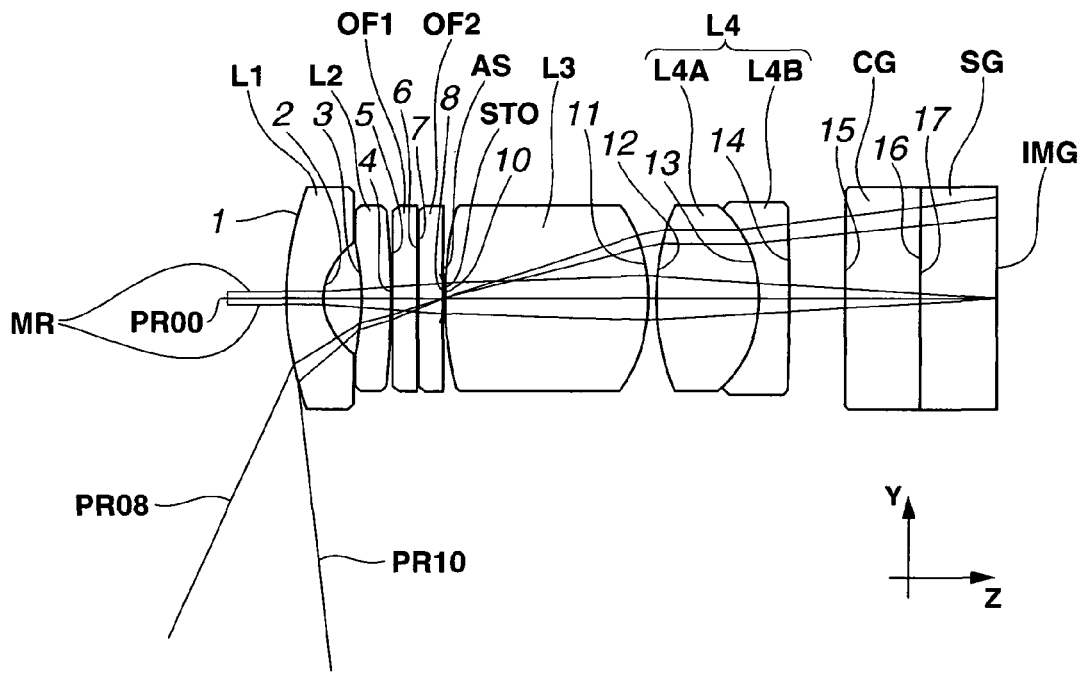
FIG. 13 is a drawing showing a configuration along an optical path of an optical system including the objective lens according to example 6 of the embodiment.
Figure 14:
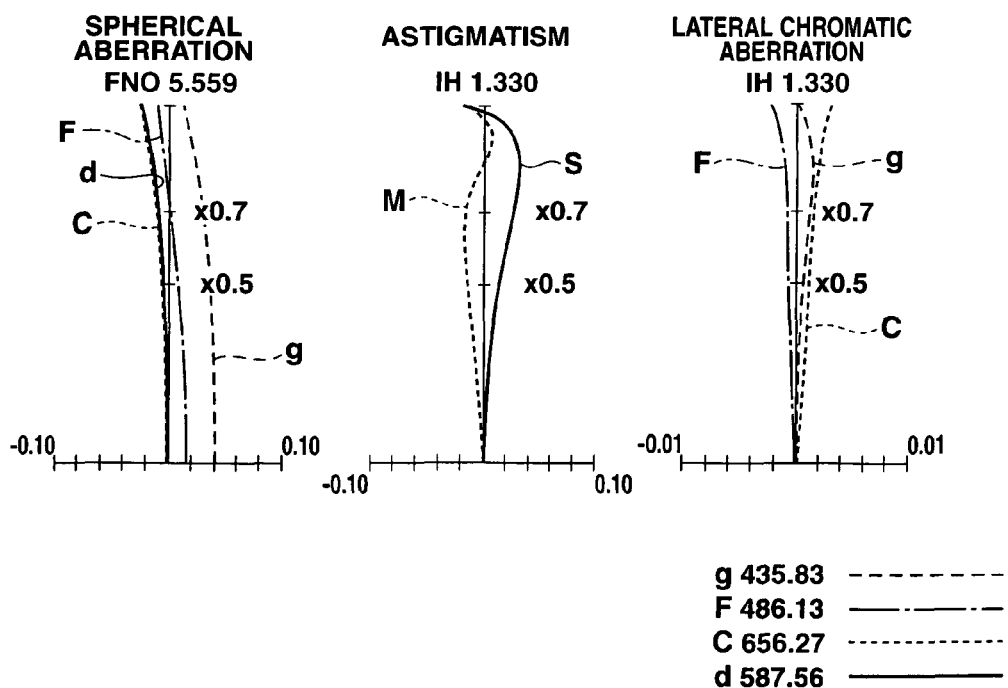
FIG. 14 is a drawing showing spherical aberration, astigmatism, and lateral chromatic aberration of the objective lens according to example 6 of the embodiment.

FIG. 13 is a drawing showing a configuration along the optical path of the optical system including the objective lens according to example 6 and FIG. 14 is a drawing showing spherical aberration, astigmatism, and lateral chromatic aberration of the objective lens according to example 6.

As shown in FIG. 13, the objective lens according to example 6 includes, in order from the object side, a first lens L1 which is a negative meniscus lens with a convex surface turned to the object side, a second lens L2 which is a negative meniscus lens with a concave surface turned to the object side, an aperture stop AS, a third lens L3 which is a double-convex lens (positive lens), and a fourth lens L4 which is a cemented lens made up of a positive, double-convex lens L4A and a negative meniscus lens L4B with a concave surface turned to the object side. The negative lens L4B in the fourth lens L4 is made of glass material K-PSFn214 with an Abbe number (vd) of 17.77. The lenses L1 and L2 make up a front group with negative refractive power while lenses L3 and L4 make up a rear group with positive refractive power.

Optical members (such as a laser cut filter, an infrared cut filter, or an optical low-pass filter) according to example 6 are placed between the second lens L2 and the aperture stop AS, and include a first optical member OF1 and a second optical member OF2 in order from the object side. On the image side of the fourth lens L4, the CCD cover glass CG and the CCD chip sealing glass SG are placed in order from the object side.

FIG. 13 shows rays including an axial marginal ray MR, a principal ray PR10 forming an image at a maximum angle of view of 193.8° at an image height ratio of 1 (an image height of 1.330), and a principal ray PR08 forming an image at an image height ratio of 0.8 (an image height of 1.330×0.8) as well as an optical axis PR00.

The spherical aberration, astigmatism, and lateral chromatic aberration are as shown in FIG. 14.

Numeric data of the optical system according to example 6 is shown below.

TABLE 6

| Surface number | Radius of curvature | Spacing | Refractive index | Abbe number vd |
|---|---|---|---|---|
| OBJ | INF | INF | 1. | |
| 1 | 4.4383 | 0.4939 | 2.17840 | 33.00 |
| 2 | 0.9162 | 0.4882 | 1. | |
| 3 | −3.3981 | 0.3952 | 1.88300 | 40.76 |
| 4 | −7.4622 | 0.0296 | 1. | |
| 5 | INF | 0.3062 | 1.51400 | 75.00 |
| 6 | INF | 0.0296 | 1. | |
| 7 | INF | 0.3062 | 1.52287 | 59.89 |
| 8 | INF | 0. | 1. | |
| STO | INF | 0.0296 | 1. | |
| 10 | 5.5964 | 2.6884 | 1.88300 | 40.76 |
| 11 | −2.1240 | 0.0988 | 1. | |
| 12 | 3.0670 | 1.3467 | 1.72916 | 54.68 |
| 13 | −1.7176 | 0.3952 | 2.14352 | 17.77 |
| 14 | −16.8211 | 0.7330 | 1. | |
| 15 | INF | 0.9879 | 1.51633 | 64.14 |
| 16 | INF | 0.0099 | 1.51000 | 64.10 |

TABLE 6-continued

| Surface number | Radius of curvature | Spacing | Refractive index | Abbe number vd |
|---|---|---|---|---|
| 17 | INF | 0.9879 | 1.61061 | 50.20 |
| IMG | INF | 0. | | |

EXAMPLE 7

Figure 15:
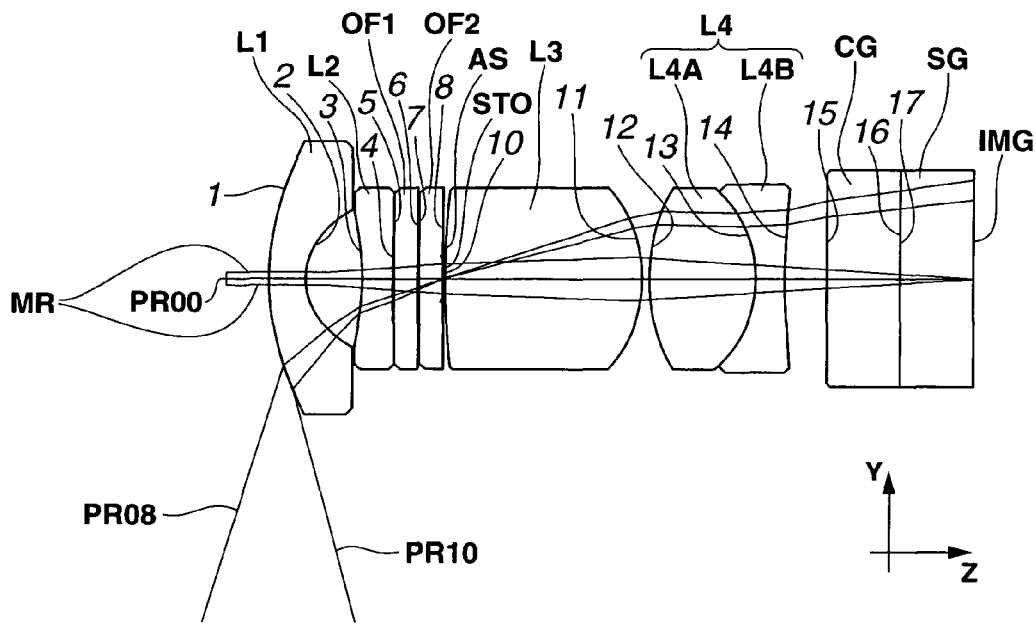
FIG. 15 is a drawing showing a configuration along an optical path of an optical system including the objective lens according to example 7 of the embodiment.
Figure 16:
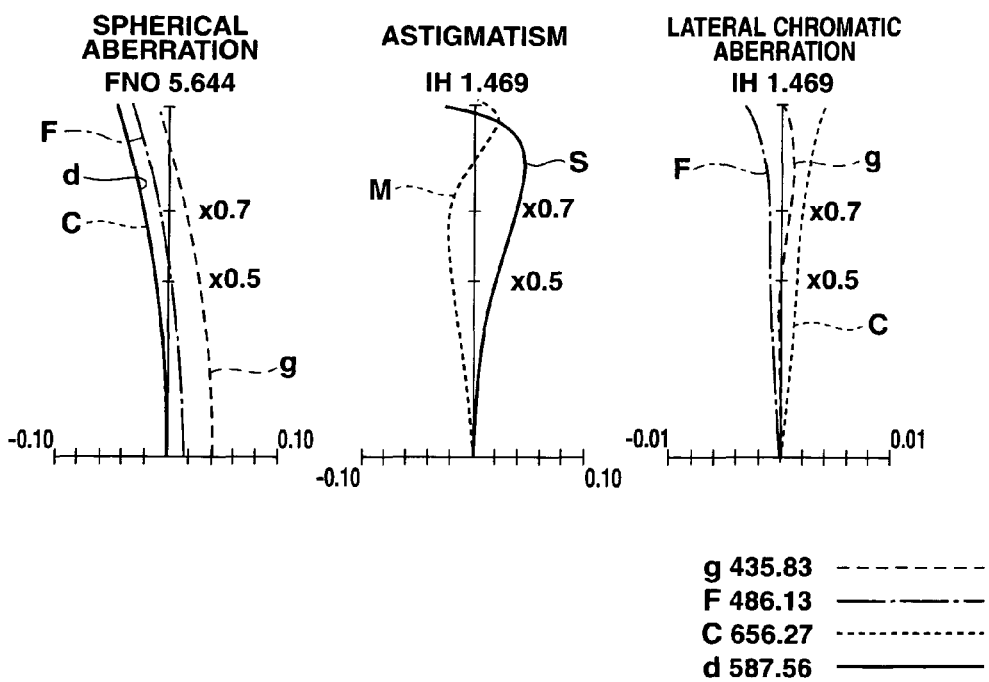
FIG. 16 is a drawing showing spherical aberration, astigmatism, and lateral chromatic aberration of the objective lens according to example 7 of the embodiment.

FIG. 15 is a drawing showing a configuration along the optical path of the optical system including the objective lens according to example 7 and FIG. 16 is a drawing showing spherical aberration, astigmatism, and lateral chromatic aberration of the objective lens according to example 7.

As shown in FIG. 15, the objective lens according to example 7 includes, in order from the object side, a first lens L1 which is a negative meniscus lens with a convex surface turned to the object side, a second lens L2 which is a double-concave lens (negative lens), an aperture stop AS, a third lens L3 which is a double-convex lens (positive lens), and a fourth lens L4 which is a cemented lens made up of a positive, double-convex lens L4A and a negative, double-concave lens L4B. The negative lens L4B in the fourth lens L4 is made of glass material K-PSFn214 with an Abbe number (vd) of 17.77. The lenses L1 and L2 make up a front group with negative refractive power while lenses L3 and L4 make up a rear group with positive refractive power.

Optical members (such as a laser cut filter, an infrared cut filter, or an optical low-pass filter) according to example 7 are placed between the second lens L2 and the aperture stop AS, and include a first optical member OF1 and a second optical member OF2 in order from the object side. On the image side of the fourth lens L4, the CCD cover glass CG and the CCD chip sealing glass SG are placed in order from the object side.

FIG. 15 shows rays including an axial marginal ray MR, a principal ray PR10 forming an image at a maximum angle of view of 211.2° at an image height ratio of 1 (an image height of 1.469), and a principal ray PR08 forming an image at an image height ratio of 0.8 (an image height of 1.469×0.8) as well as an optical axis PR00.

The spherical aberration, astigmatism, and lateral chromatic aberration are as shown in FIG. 16.

Numeric data of the optical system according to example 7 is shown below.

TABLE 7

| Surface number | Radius of curvature | Spacing | Refractive index | Abbe number vd |
|---|---|---|---|---|
| OBJ | INF | INF | 1. | |
| 1 | 4.1535 | 0.5458 | 2.17840 | 33.00 |
| 2 | 1.0714 | 0.8439 | 1. | |
| 3 | −4.5738 | 0.4367 | 1.88300 | 40.76 |
| 4 | 69.2005 | 0.0328 | 1. | |
| 5 | INF | 0.3384 | 1.51400 | 75.00 |
| 6 | INF | 0.0328 | 1. | |
| 7 | INF | 0.3384 | 1.52287 | 59.89 |
| 8 | INF | 0. | 1. | |
| STO | INF | 0.0328 | 1. | |
| 10 | 11.7978 | 2.8645 | 1.88300 | 40.76 |
| 11 | −2.1107 | 0.1092 | 1. | |
| 12 | 2.8808 | 1.5236 | 1.72916 | 54.68 |
| 13 | −1.9423 | 0.4367 | 2.14352 | 17.77 |
| 14 | 20.1858 | 0.6054 | 1. | |
| 15 | INF | 1.0917 | 1.51633 | 64.14 |
| 16 | INF | 0.0109 | 1.51000 | 64.10 |
| 17 | INF | 1.0917 | 1.61061 | 50.20 |
| IMG | INF | 0. | | |

EXAMPLE 8

Figure 17:
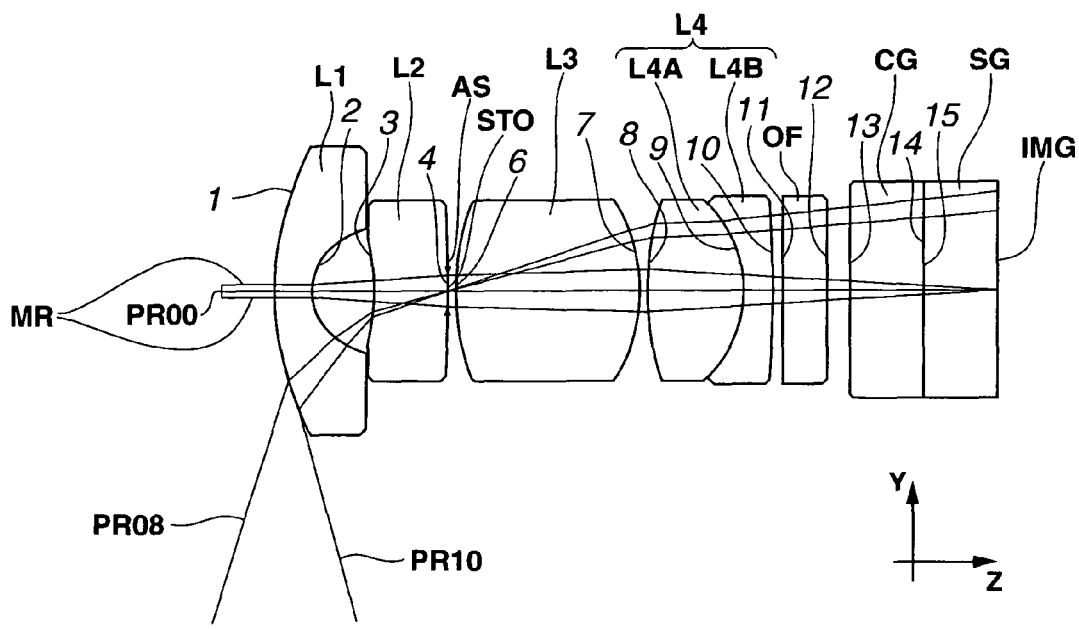
FIG. 17 is a drawing showing a configuration along an optical path of an optical system including the objective lens according to example 8 of the embodiment.
Figure 18:
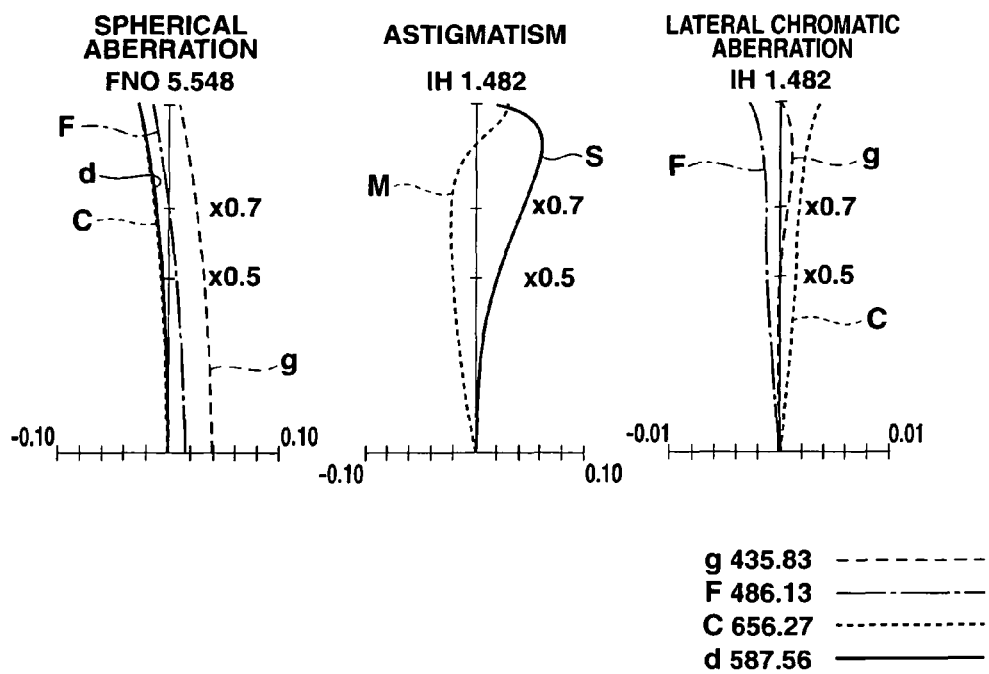
FIG. 18 is a drawing showing spherical aberration, astigmatism, and lateral chromatic aberration of the objective lens according to example 8 of the embodiment.

FIG. 17 is a drawing showing a configuration along the optical path of the optical system including the objective lens according to example 8 and FIG. 18 is a drawing showing spherical aberration, astigmatism, and lateral chromatic aberration of the objective lens according to example 8.

As shown in FIG. 17, the objective lens according to example 8 includes, in order from the object side, a first lens L1 which is a negative meniscus lens with a convex surface turned to the object side, a second lens L2 which is a negative meniscus lens with a concave surface turned to the object side, an aperture stop AS, a third lens L3 which is a double-convex lens (positive lens), and a fourth lens L4 which is a cemented lens made up of a positive, double-convex lens L4A and a negative meniscus lens L4B with a concave surface turned to the object side. Among these lenses, the first lens L1 has an aspherical surface on the image side and the aspherical shape of the image-side surface is configured such that the negative refractive power will decrease with distance from the optical axis. The negative lens L4B in the fourth lens L4 is made of glass material K-PSFn214 with an Abbe number (vd) of 17.77. The lenses L1 and L2 make up a front group with negative refractive power while lenses L3 and L4 make up a rear group with positive refractive power.

On the image side of the fourth lens L4, the above-described optical member OF, CCD cover glass CG, and CCD chip sealing glass SG are placed in order from the object side.

FIG. 17 shows rays including an axial marginal ray MR, a principal ray PR10 forming an image at a maximum angle of view of 209.6° at an image height ratio of 1 (an image height of 1.482), and a principal ray PR08 forming an image at an image height ratio of 0.8 (an image height of 1.482×0.8) as well as an optical axis PR00.

The spherical aberration, astigmatism, and lateral chromatic aberration are as shown in FIG. 18.

Numeric data of the optical system according to example 8 is shown below.

TABLE 8

| Surface number | Radius of curvature | Spacing | Refractive index | Abbe number vd |
|---|---|---|---|---|
| OBJ | INF | INF | 1. | |
| 1 | 4.6641 | 0.5506 | 1.88300 | 40.76 |
| 2$ | 0.8911 | 0.9648 | 1. | |
| 3 | −2.6962 | 1.0823 | 1.88300 | 40.76 |
| 4 | −39.3243 | 0.0220 | 1. | |
| STO | INF | 0.1071 | 1. | |
| 6 | 4.0415 | 2.7762 | 1.88300 | 40.76 |
| 7 | −2.7045 | 0.1101 | 1. | |
| 8 | 3.5956 | 1.5016 | 1.72916 | 54.68 |
| 9 | −1.8683 | 0.4405 | 2.14352 | 17.77 |
| 10 | −7.6667 | 0.1432 | 1. | |
| 11 | INF | 0.6608 | 1.51800 | 75.00 |
| 12 | INF | 0.3409 | 1. | |
| 13 | INF | 1.1013 | 1.51633 | 64.14 |
| 14 | INF | 0.0110 | 1.51000 | 64.10 |
| 15 | INF | 1.1013 | 1.61061 | 50.20 |
| IMG | INF | 0. | | |
| S2 ASP | RDY 0.8911 | K −0.1465 | | |
| | AC2 0.0000E+00 | AC4 −9.6839E−03 | AC6 2.3249E−02 | AC8 0.0000E+00 | AC10 0.0000E+00 |

EXAMPLE 9

Figure 19:
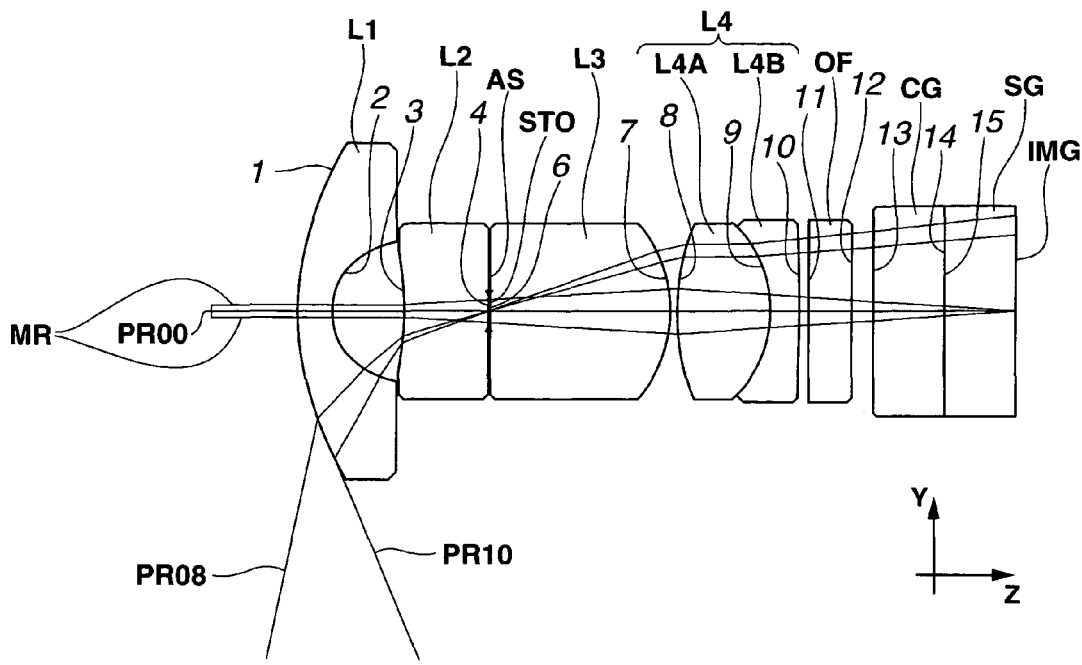
FIG. 19 is a drawing showing a configuration along an optical path of an optical system including the objective lens according to example 9 of the embodiment.
Figure 20:
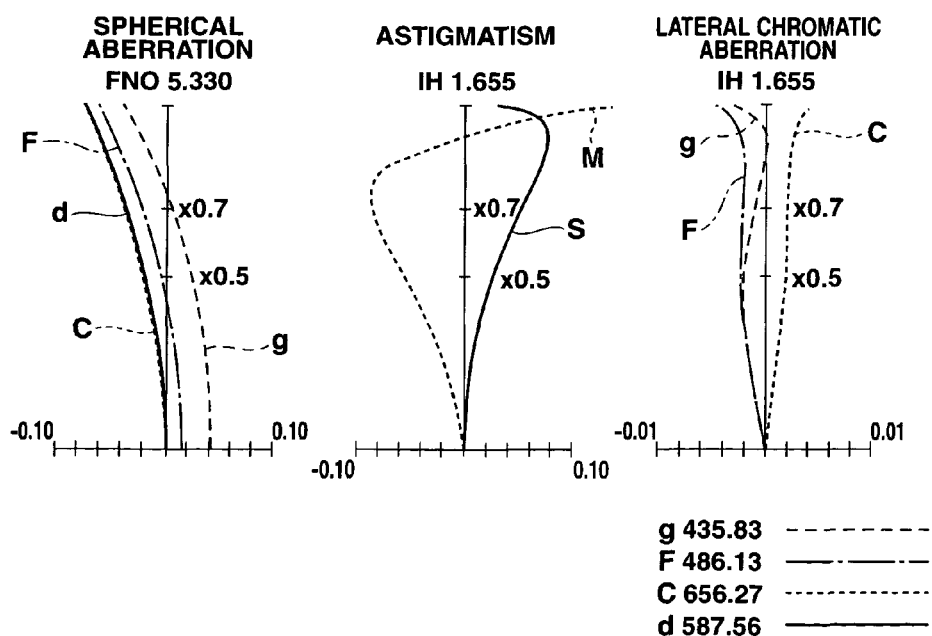
FIG. 20 is a drawing showing spherical aberration, astigmatism, and lateral chromatic aberration of the objective lens according to example 9 of the embodiment.
Figure 21:
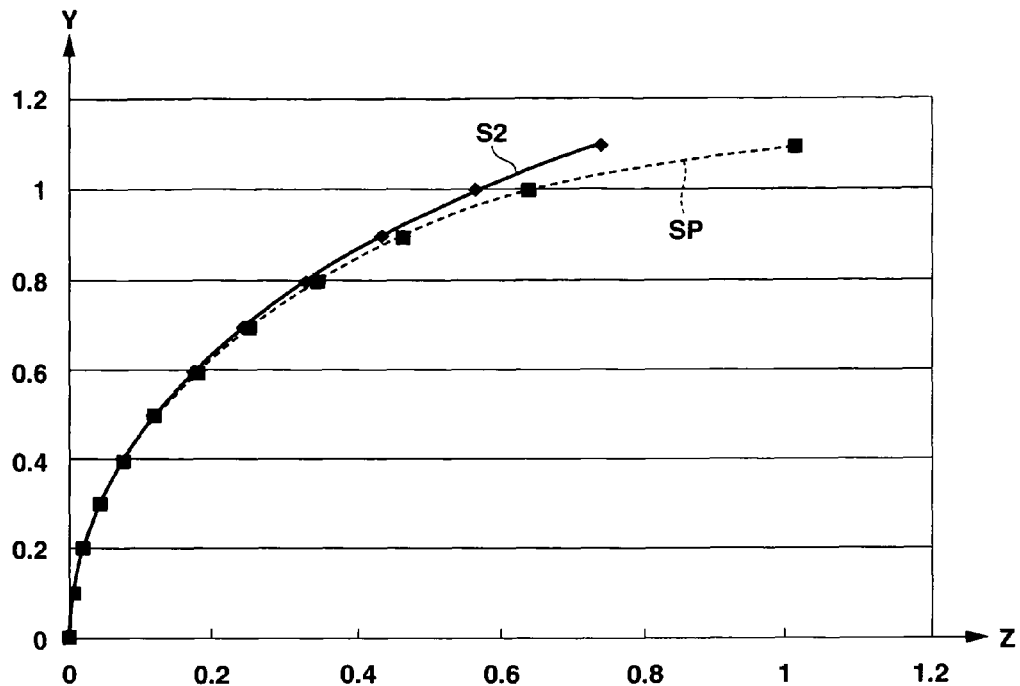
FIG. 21 is a diagram showing an aspherical shape of an image-side surface of a first lens of the objective lens according to example 9 of the embodiment.

FIG. 19 is a drawing showing a configuration along the optical path of the optical system including the objective lens according to example 9, FIG. 20 is a drawing showing spherical aberration, astigmatism, and lateral chromatic aberration of the objective lens according to example 9, and FIG. 21 is a diagram showing an aspherical shape of an image-side surface of a first lens of the objective lens.

As shown in FIG. 19, the objective lens according to example 9 includes, in order from the object side, a first lens L1 which is a negative meniscus lens with a convex surface turned to the object side, a second lens L2 which is a plano-concave lens (negative lens) with a concave surface turned to the object side, an aperture stop AS, a third lens L3 which is a plano-convex lens (positive lens) with a convex surface turned to the image side, and a fourth lens L4 which is a cemented lens made up of a positive, double-convex lens L4A and a negative, plano-concave lens with a concave surface turned to the object side. The negative lens L4B in the fourth lens L4 has an Abbe number (vd) of 18.90. The lenses L1 and L2 make up a front group with negative refractive power while lenses L3 and L4 make up a rear group with positive refractive power.

The objective lens according to example 9 has only one aspherical surface, namely surface No. 2 on the image side of the first lens L1. More specifically, surface No. 2 on the image side of the first lens L1 (denoted by reference character S2 in FIG. 21) is an aspherical surface configured such that the negative refractive power will decrease with distance from the optical axis as shown in FIG. 21 which is a comparative diagram for comparison with a reference spherical surface SP.

On the image side of the fourth lens L4, the above-described optical member OF, CCD cover glass CG, and CCD chip sealing glass SG are placed in order from the object side.

FIG. 19 shows rays including an axial marginal ray MR, a principal ray PR10 forming an image at a maximum angle of view of 223.3° at an image height ratio of 1 (an image height of 1.655), and a principal ray PR08 forming an image at an image height ratio of 0.8 (an image height of 1.655×0.8) as well as an optical axis PR00.

The spherical aberration, astigmatism, and lateral chromatic aberration are as shown in FIG. 20.

Numeric data of the optical system according to example 9 is shown below.

TABLE 9

| Surface number | Radius of curvature | Spacing | Refractive index | Abbe number vd |
|---|---|---|---|---|
| OBJ | INF | INF | 1. | |
| 1 | 5.0824 | 0.6147 | 1.88300 | 40.76 |
| 2$ | 1.1040 | 1.2751 | 1. | |
| 3 | −3.4470 | 1.4429 | 1.88300 | 40.76 |
| 4 | INF | 0.0246 | 1. | |
| STO | INF | 0.0431 | 1. | |
| 6 | INF | 3.0753 | 1.88300 | 40.76 |
| 7 | −2.2633 | 0.1229 | 1. | |
| 8 | 4.5840 | 1.6474 | 1.72916 | 54.68 |
| 9 | −2.0610 | 0.4918 | 1.92286 | 18.90 |
| 10 | INF | 0.1598 | 1. | |
| 11 | INF | 0.7377 | 1.51800 | 75.00 |
| 12 | INF | 0.4091 | 1. | |
| 13 | INF | 1.2294 | 1.51633 | 64.14 |
| 14 | INF | 0.0123 | 1.51000 | 64.10 |
| 15 | INF | 1.2294 | 1.61061 | 50.20 |
| IMG | INF | 0. | | |
| S2 ASP | RDY | K | | |
| | 1.1040 | −0.2300 | | |
| AC2 | AC4 | AC6 | AC8 | AC10 |
| 0.0000E+00 | 0.0000E+00 | 0.0000E+00 | 0.0000E+00 | 0.0000E+00 |

EXAMPLE 10

Figure 22:
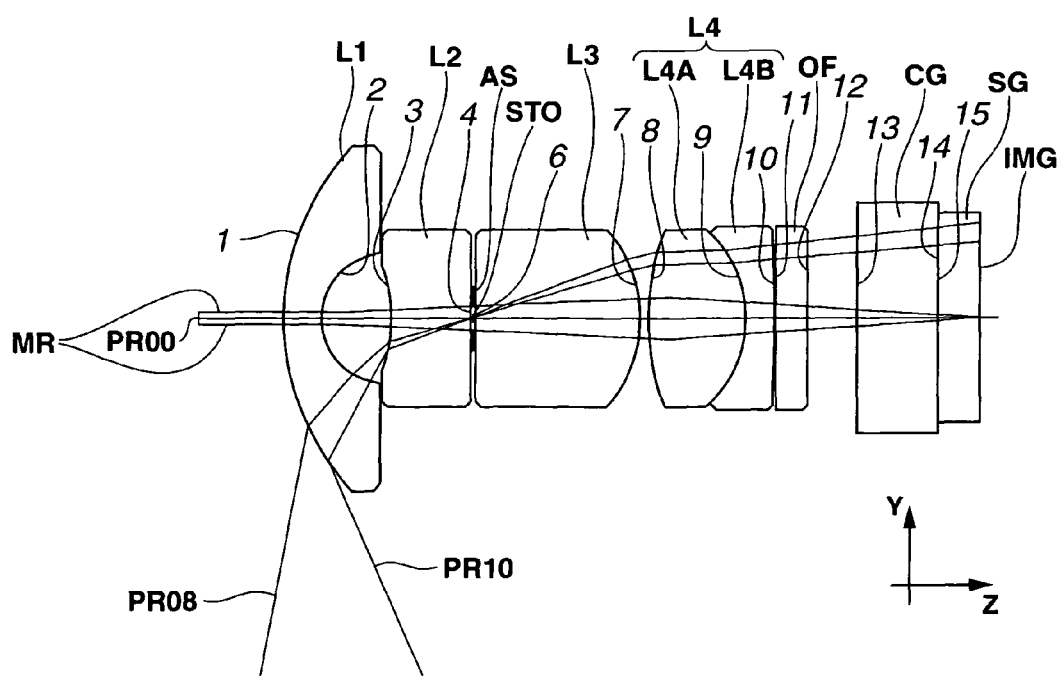
FIG. 22 is a drawing showing a configuration along an optical path of an optical system including the objective lens according to example 10 of the embodiment.
Figure 23:
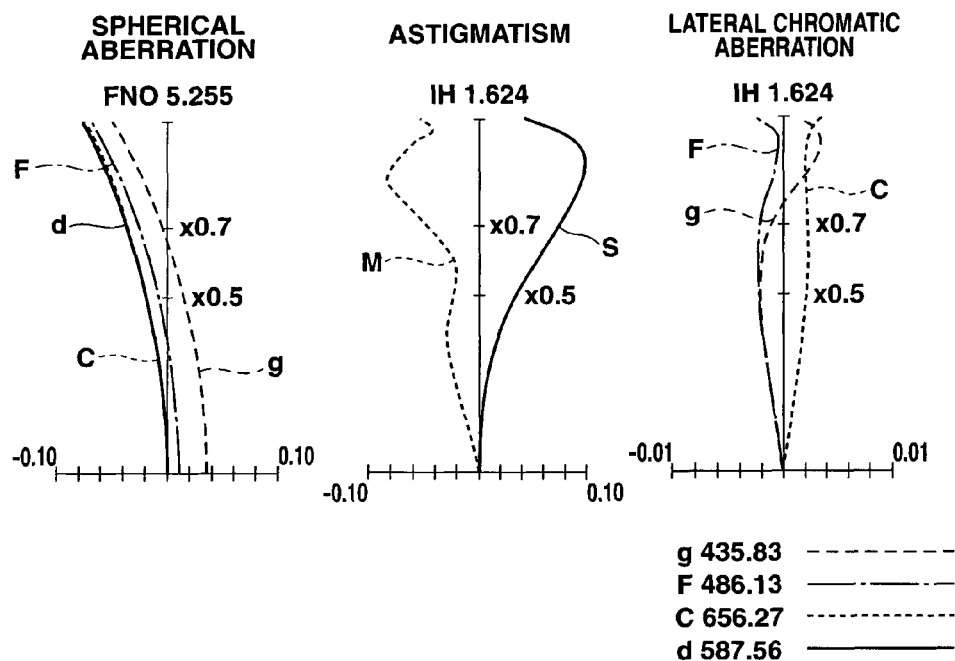
FIG. 23 is a drawing showing spherical aberration, astigmatism, and lateral chromatic aberration of the objective lens according to example 10 of the embodiment.
Figure 24:
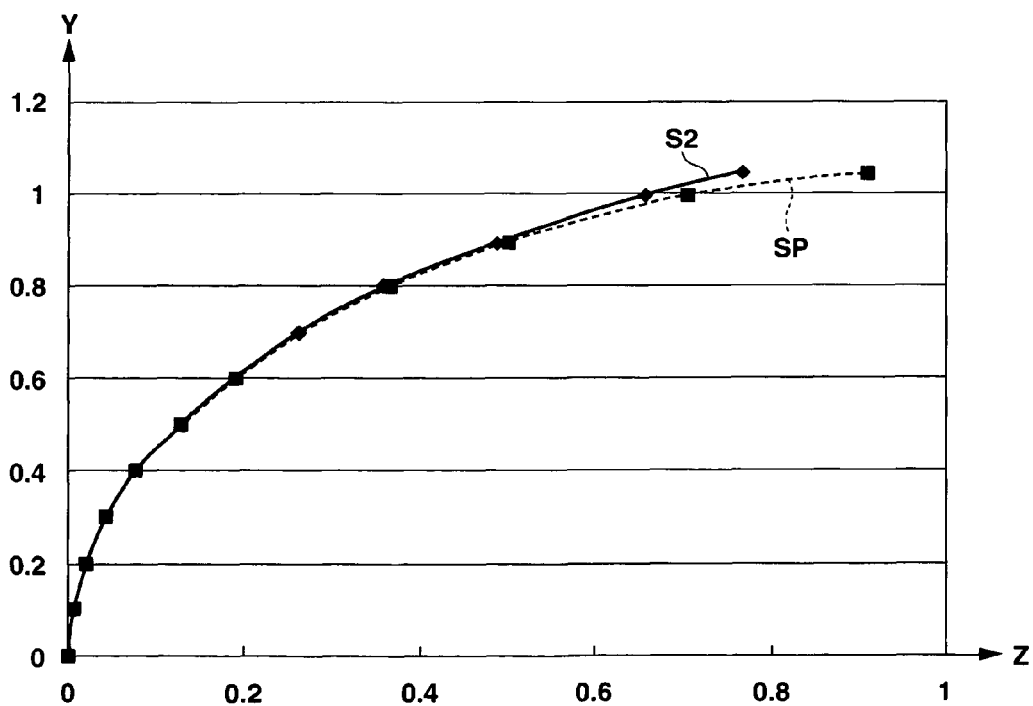
FIG. 24 is a diagram showing an aspherical shape of an image-side surface of a first lens of the objective lens according to example 10 of the embodiment.

FIG. 22 is a drawing showing a configuration along the optical path of the optical system including the objective lens according to example 10, FIG. 23 is a drawing showing spherical aberration, astigmatism, and lateral chromatic aberration of the objective lens according to example 10, and FIG. 24 is a diagram showing an aspherical shape of an image-side surface of a first lens of the objective lens.

As shown in FIG. 22, the objective lens according to example 10 includes, in order from the object side, a first lens L1 which is a negative meniscus lens with a convex surface turned to the object side, a second lens L2 which is a plano-concave lens (negative lens) with a concave surface turned to the object side, an aperture stop AS, a third lens L3 which is a plano-convex lens (positive lens) with a convex surface turned to the image side, and a fourth lens L4 which is a cemented lens made up of a positive, double-convex lens L4A and a negative, plano-concave lens L4B with a concave surface turned to the object side. The negative lens L4B in the fourth lens L4 has an Abbe number (vd) of 18.90. The lenses L1 and L2 make up a front group with negative refractive power while lenses L3 and L4 make up a rear group with positive refractive power.

The objective lens according to example 10 has two aspherical surfaces: surface No. 1 on the object side of the first lens L1 and surface No. 2 on the image side of the first lens L1. Surface No. 2 on the object side of the first lens L1 (denoted by reference character S2 in FIG. 24) is an aspherical surface configured such that the negative refractive power will decrease with distance from the optical axis as shown in FIG. 24 which is a comparative diagram for comparison with the reference spherical surface SP.

On the image side of the fourth lens L4, the above-described optical member OF, CCD cover glass CG, and CCD chip sealing glass SG are placed in order from the object side.

FIG. 22 shows rays including an axial marginal ray MR, a principal ray PR10 forming an image at a maximum angle of view at an image height ratio of 1 (an image height of 1.624), and a principal ray PR08 forming an image at an image height ratio of 0.8 (an image height of 1.624×0.8) as well as an optical axis PR00.

The spherical aberration, astigmatism, and lateral chromatic aberration are as shown in FIG. 23.

Numeric data of the optical system according to example 10 is shown below.

TABLE 10

| Surface number | Radius of curvature | Spacing | Refractive index | Abbe number vd |
|---|---|---|---|---|
| OBJ | INF | INF | 1. | |
| 1$ | 4.7434 | 0.6033 | 1.88300 | 40.76 |
| 2$ | 1.0609 | 1.1593 | 1. | |
| 3 | −2.9850 | 1.3002 | 1.88300 | 40.76 |
| 4 | INF | 0.0241 | 1. | |
| STO | INF | 0.0562 | 1. | |
| 6 | INF | 2.8387 | 1.88300 | 40.76 |
| 7 | −2.1613 | 0.1207 | 1. | |
| 8 | 4.3297 | 1.6284 | 1.72916 | 54.68 |
| 9 | −2.0344 | 0.4827 | 1.92286 | 18.90 |
| 10 | INF | 0.0535 | 1. | |
| 11 | INF | 0.5349 | 1.51800 | 75.01 |
| 12 | INF | 0.8311 | 1. | |
| 13 | INF | 1.3372 | 1.51633 | 64.14 |

TABLE 10-continued

| Surface number | Radius of curvature | Spacing | Refractive index | Abbe number vd |
|---|---|---|---|---|
| 14 | INF | 0.0178 | 1.51000 | 63.01 |
| 15 | INF | 0.7132 | 1.61061 | 50.20 |
| IMG | INF | 0. | | |
| S1 ASP | RDY 4.7434 | K −6.0989 | | |
| AC2 0.0000E+00 | AC4 1.1705E−02 | AC6 −1.4349E−03 | AC8 8.7443E−05 | AC10 0.0000E+00 |
| S2 ASP | RDY 1.0609 | K −0.9713 | | |
| AC2 0.0000E+00 | AC4 9.3600E−02 | AC6 1.8642E−02 | AC8 6.8257E−02 | AC10 0.0000E+00 |

EXAMPLE 11

Figure 25:
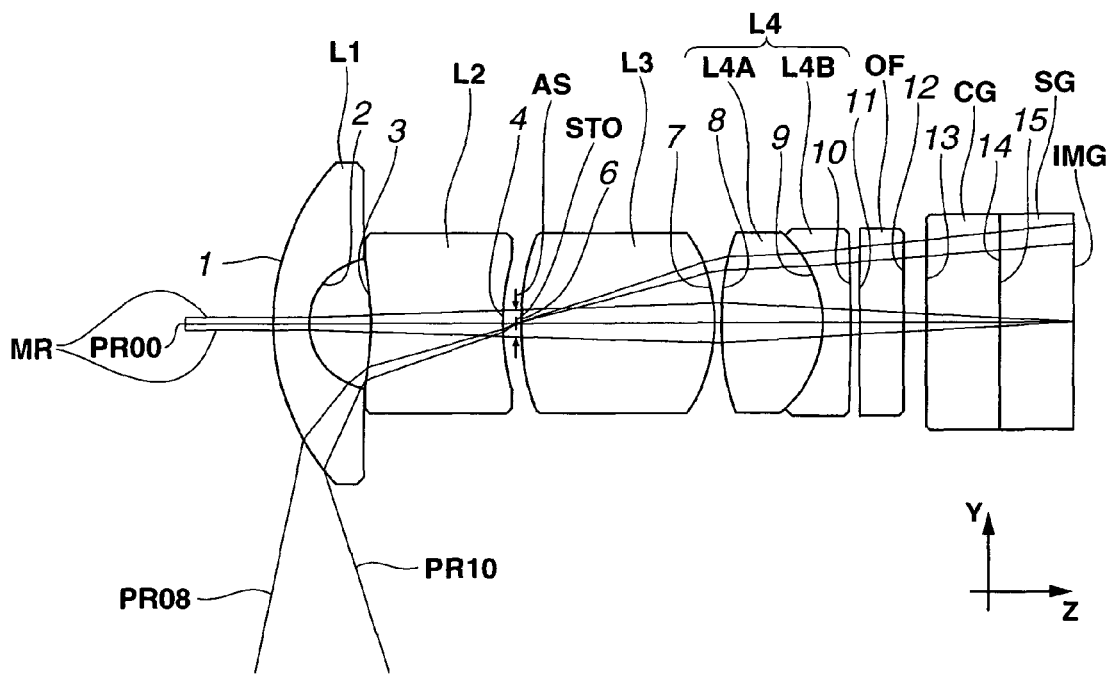
FIG. 25 is a drawing showing a configuration along an optical path of an optical system including the objective lens according to example 11 of the embodiment.
Figure 26:
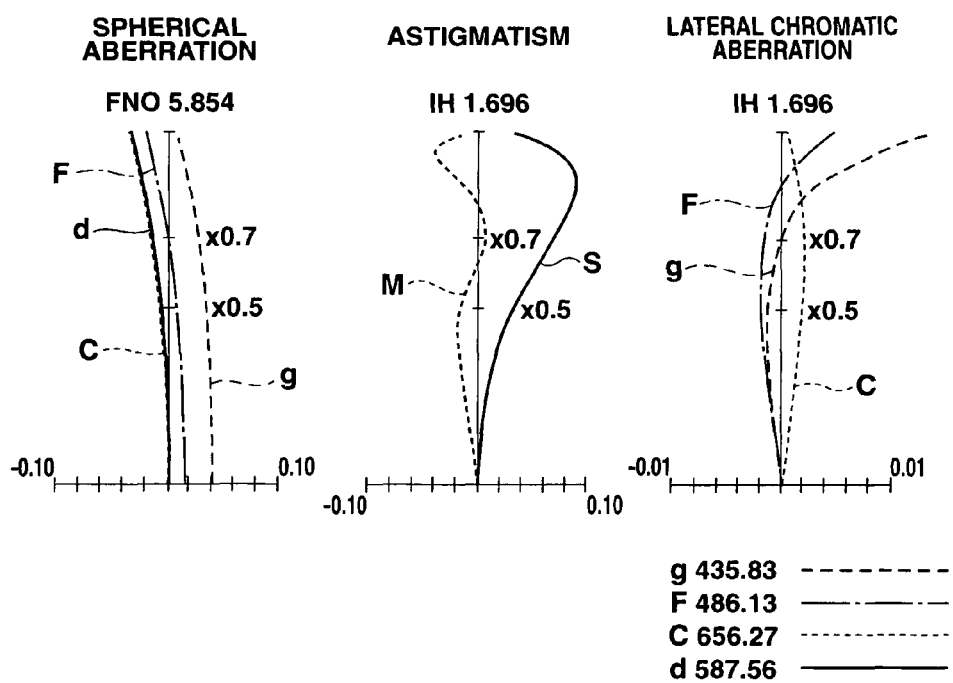
FIG. 26 is a drawing showing spherical aberration, astigmatism, and lateral chromatic aberration of the objective lens according to example 11 of the embodiment.
Figure 27:
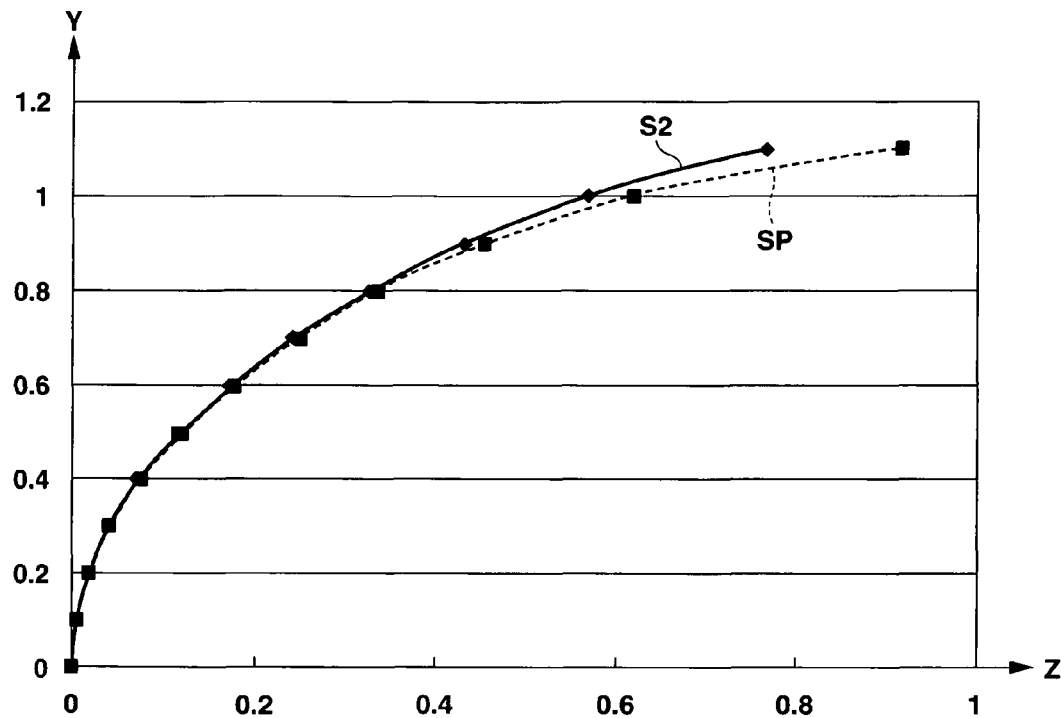
FIG. 27 is a diagram showing an aspherical shape of an image-side surface of a first lens of the objective lens according to example 11 of the embodiment.

FIG. 25 is a drawing showing a configuration along the optical path of the optical system including the objective lens according to example 11, FIG. 26 is a drawing showing spherical aberration, astigmatism, and lateral chromatic aberration of the objective lens according to example 11, and FIG. 27 is a diagram showing an aspherical shape of an image-side surface of a first lens of the objective lens.

As shown in FIG. 25, the objective lens according to example 11 includes, in order from the object side, a first lens L1 which is a negative meniscus lens with a convex surface turned to the object side, a second lens L2 which is a double-concave lens (i.e., a negative lens with a concave surface turned to the object side), an aperture stop AS, a third lens L3 which is a double-convex lens (positive lens), and a fourth lens L4 which is a cemented lens made up of a positive, double-convex lens L4A and a negative meniscus lens L4B with a convex surface turned to the image side. The negative lens L4B in the fourth lens L4 has an Abbe number (vd) of 18.90. The lenses L1 and L2 make up a front group with negative refractive power while lenses L3 and L4 make up a rear group with positive refractive power.

The objective lens according to example 11 has only one aspherical surface, namely surface No. 2 on the image side of the first lens L1. Surface No. 2 on the image side of the first lens L1 (denoted by reference character S2 in FIG. 27) is an aspherical surface configured such that the negative refractive power will decrease with distance from the optical axis as shown in FIG. 27 which is a comparative diagram for comparison with the reference spherical surface SP.

On the image side of the fourth lens L4, the above-described optical member OF, CCD cover glass CG, and CCD chip sealing glass SG are placed in order from the object side.

FIG. 25 shows rays including an axial marginal ray MR, a principal ray PR10 forming an image at a maximum angle of view at an image height ratio of 1 (an image height of 1.696), and a principal ray PR08 forming an image at an image height ratio of 0.8 (an image height of 1.696×0.8) as well as an optical axis PR00.

The spherical aberration, astigmatism, and lateral chromatic aberration are as shown in FIG. 26.

Numeric data of the optical system according to example 11 is shown below.

TABLE 11

| Surface number | Radius of curvature | Spacing | Refractive index | Abbe number vd |
|---|---|---|---|---|
| OBJ | INF | INF | 1. | |
| 1 | 4.4007 | 0.6300 | 1.88300 | 40.76 |
| 2$ | 1.1182 | 1.0858 | 1. | |

TABLE 11-continued

| Surface number | Radius of curvature | Spacing | Refractive index | Abbe number vd |
|---|---|---|---|---|
| 3 | −5.3310 | 2.2932 | 1.88300 | 40.76 |
| 4 | 4.3741 | 0.2532 | 1. | |
| STO | INF | 0.0738 | 1. | |
| 6 | 4.8829 | 3.3994 | 1.88300 | 40.76 |
| 7 | −2.8751 | 0.1260 | 1. | |
| 8 | 4.8246 | 1.8648 | 1.72916 | 54.68 |
| 9 | −1.9824 | 0.5040 | 1.92286 | 18.90 |
| 10 | −24.3537 | 0.1638 | 1. | |
| 11 | INF | 0.7560 | 1.51800 | 75.00 |
| 12 | INF | 0.4063 | 1. | |
| 13 | INF | 1.2600 | 1.51633 | 64.14 |
| 14 | INF | 0.0126 | 1.51000 | 64.10 |
| 15 | INF | 1.2600 | 1.61061 | 50.20 |
| IMG | INF | 0. | | |
| S2 ASP | RDY 1.1182 | K −0.1045 | | |
| AC2 0.0000E+00 | AC4 −6.8198E−03 | AC6 −8.1051E−03 | AC8 0.0000E+00 | AC10 0.0000E+00 |

EXAMPLE 12

Figure 28:
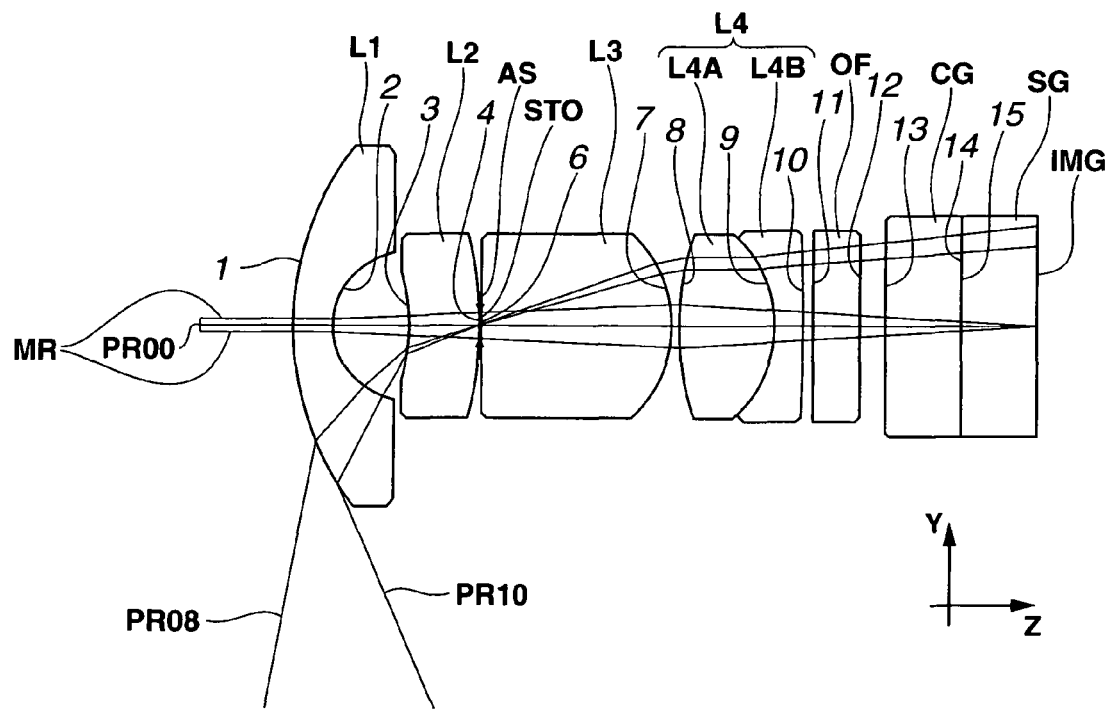
FIG. 28 is a drawing showing a configuration along an optical path of an optical system including the objective lens according to example 12 of the embodiment.
Figure 29:
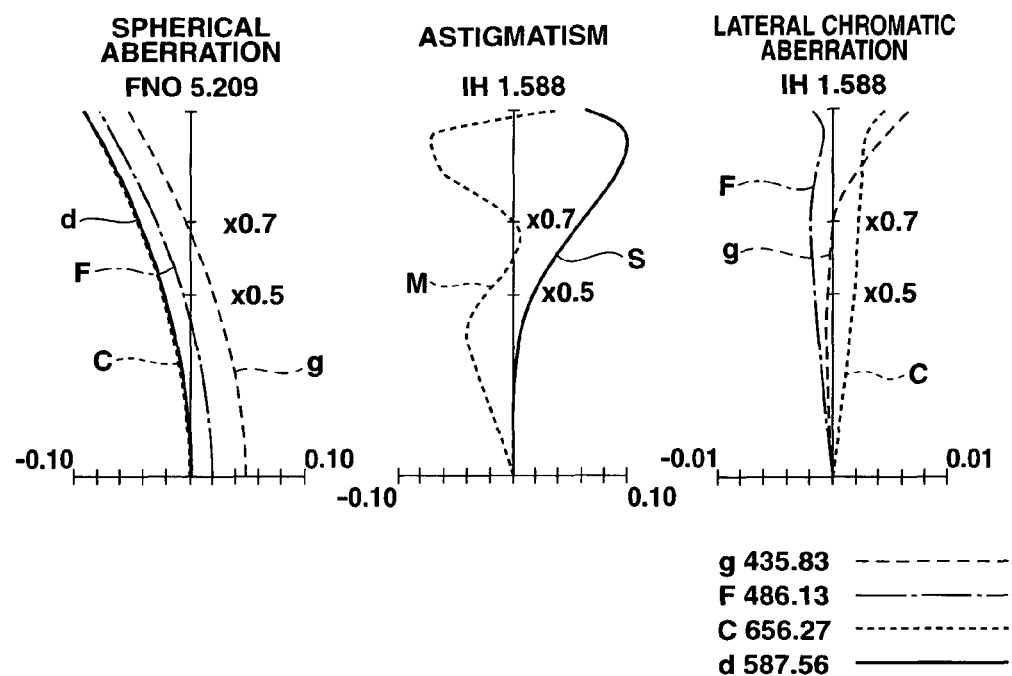
FIG. 29 is a drawing showing spherical aberration, astigmatism, and lateral chromatic aberration of the objective lens according to example 12 of the embodiment.
Figure 30:
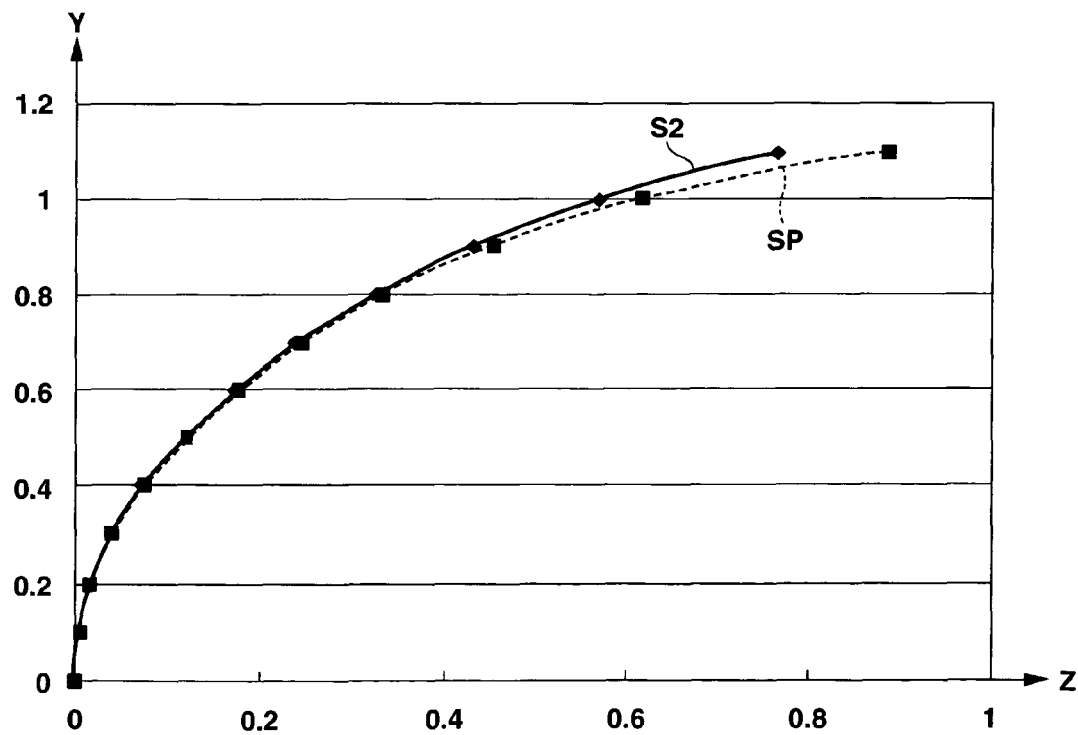
FIG. 30 is a diagram showing an aspherical shape of an image-side surface of a first lens of the objective lens according to example 12 of the embodiment.

FIG. 28 is a drawing showing a configuration along the optical path of the optical system including the objective lens according to example 12, FIG. 29 is a drawing showing spherical aberration, astigmatism, and lateral chromatic aberration of the objective lens according to example 12, and FIG. 30 is a diagram showing an aspherical shape of an image-side surface of a first lens of the objective lens.

As shown in FIG. 28, the objective lens according to example 12 includes, in order from the object side, a first lens L1 which is a negative meniscus lens with a convex surface turned to the object side, a second lens L2 which is a negative meniscus lens with a concave surface turned to the object side and a convex surface turned to the image side, an aperture stop AS, a third lens L3 which is a plano-convex lens (positive lens) with a convex surface turned to the image side, and a fourth lens L4 which is a cemented lens made up of a positive, double-convex lens L4A and a negative meniscus lens L4B with a convex surface turned to the image side. The negative lens L4B in the fourth lens L4 has an Abbe number (vd) of 17.77. The lenses L1 and L2 make up a front group with negative refractive power while lenses L3 and L4 make up a rear group with positive refractive power.

The objective lens according to example 12 has two aspherical surfaces: surface No. 2 on the image side of the first lens L1 and surface No. 3 on the object side of the second lens L2. Surface No. 2 on the image side of the first lens L1 (denoted by reference character S2 in FIG. 30) is an aspherical surface configured such that the negative refractive power will decrease with distance from the optical axis as shown in FIG. 30 which is a comparative diagram for comparison with the reference spherical surface SP.

On the image side of the fourth lens L4, the above-described optical member OF, CCD cover glass CG, and CCD chip sealing glass SG are placed in order from the object side.

FIG. 28 shows rays including an axial marginal ray MR, a principal ray PR10 forming an image at a maximum angle of view at an image height ratio of 1 (an image height of 1.588), and a principal ray PR08 forming an image at an image height ratio of 0.8 (an image height of 1.588×0.8) as well as an optical axis PR00.

The spherical aberration, astigmatism, and lateral chromatic aberration are as shown in FIG. 29.

Numeric data of the optical system according to example 12 is shown below.

TABLE 12

| Surface number | Radius of curvature | Spacing | Refractive index | Abbe number vd |
|---|---|---|---|---|
| OBJ | INF | INF | 1. | |
| 1 | 4.6117 | 0.5899 | 1.88300 | 40.76 |
| 2$ | 1.1255 | 1.2292 | 1. | |
| 3$ | −2.0754 | 1.0722 | 1.88300 | 40.76 |
| 4 | −8.1940 | 0.0214 | 1. | |
| STO | INF | 0.0249 | 1. | |
| 6 | INF | 2.9599 | 1.88300 | 40.76 |
| 7 | −2.0723 | 0.1180 | 1. | |
| 8 | 4.3612 | 1.4876 | 1.72916 | 54.68 |
| 9 | −2.1221 | 0.4719 | 2.14352 | 17.77 |
| 10 | −13.9888 | 0.1534 | 1. | |
| 11 | INF | 0.7079 | 1.51800 | 75.00 |
| 12 | INF | 0.3736 | 1. | |
| 13 | INF | 1.1799 | 1.51633 | 64.14 |
| 14 | INF | 0.0118 | 1.51000 | 64.10 |
| 15 | INF | 1.1799 | 1.61061 | 50.20 |
| IMG | INF | 0. | | |
| S2 ASP | RDY | K | | |
| | 1.1255 | −2.3547 | | |
| AC2 | AC4 | AC6 | AC8 | AC10 |
| 0.0000E+00 | 1.8660E−01 | −5.9059E−02 | 8.0699E−02 | 0.0000E+00 |
| S3 ASP | RDY | K | | |
| | −2.0754 | 0. | | |
| AC2 | AC4 | AC6 | AC8 | AC10 |
| 0.0000E+00 | 5.5727E−02 | 8.2060E−03 | 0.0000E+00 | 0.0000E+00 |

EXAMPLE 13

Figure 33:
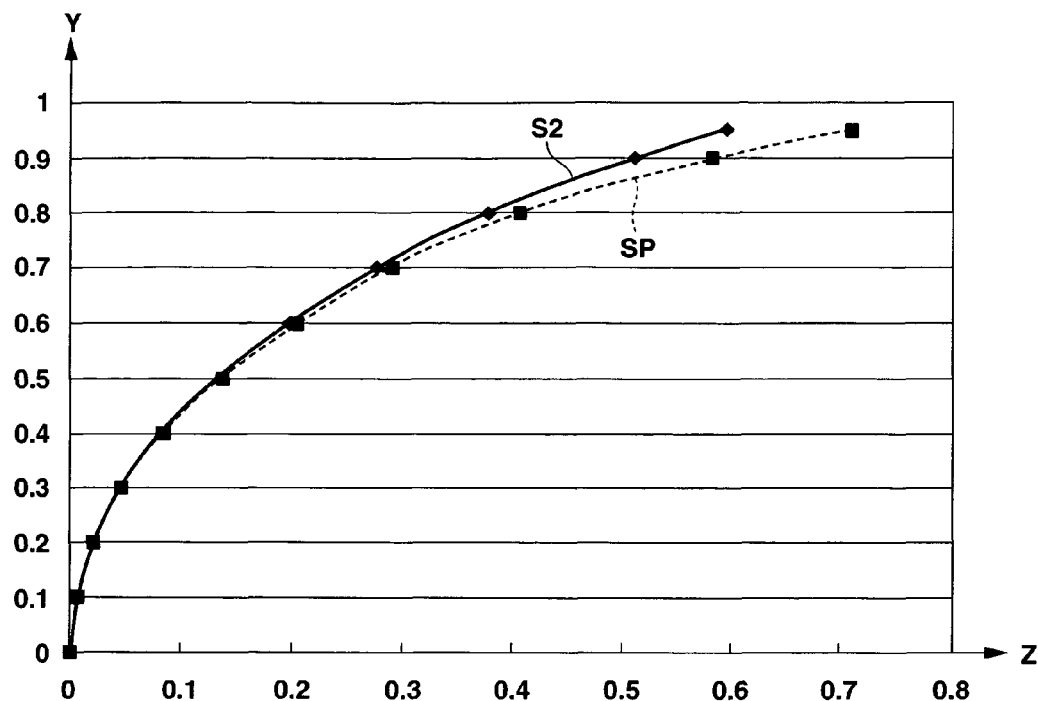
FIG. 33 is a diagram showing an aspherical shape of an image-side surface of a first lens of the objective lens according to example 13 of the embodiment.

FIG. 31 is a drawing showing a configuration along the optical path of the optical system including the objective lens according to example 13, FIG. 32 is a drawing showing spherical aberration, astigmatism, and lateral chromatic aberration of the objective lens according to example 13, and FIG. 33 is a diagram showing an aspherical shape of an image-side surface of a first lens of the objective lens.

As shown in FIG. 31, the objective lens according to example 13 includes, in order from the object side, a first lens L1 which is a negative meniscus lens with a convex surface turned to the object side, a second lens L2 which is a negative meniscus lens with a concave surface turned to the object side and a convex surface turned to the image side, an aperture stop AS, a third lens L3 which is a double-convex lens (positive lens), and a fourth lens L4 which is a cemented lens made up of a positive, double-convex lens L4A and a negative meniscus lens L4B with a convex surface turned to the image side. The negative lens L4B in the fourth lens L4 has an Abbe number (vd) of 17.77. The lenses L1 and L2 make up a front group with negative refractive power while lenses L3 and L4 make up a rear group with positive refractive power.

The objective lens according to example 13 has two aspherical surfaces: surface No. 2 on the image side of the first lens L1 and surface No. 10 on the image side of the negative meniscus lens L4B. Surface No. 2 on the image side of the first lens L1 (denoted by reference character S2 in FIG. 33) is an aspherical surface configured such that the negative refractive power will decrease with distance from the optical axis as shown in FIG. 33 which is a comparative diagram for comparison with the reference spherical surface SP.

On the image side of the fourth lens L4, the above-described optical member OF, CCD cover glass CG, and CCD chip sealing glass SG are placed in order from the object side.

FIG. 31 shows rays including an axial marginal ray MR, a principal ray PR10 forming an image at a maximum angle of view at an image height ratio of 1 (an image height of 1.569), and a principal ray PR08 forming an image at an image height ratio of 0.8 (an image height of 1.569×0.8) as well as an optical axis PR00.

The spherical aberration, astigmatism, and lateral chromatic aberration are as shown in FIG. 32.

Numeric data of the optical system according to example 13 is shown below.

TABLE 13

| Surface number | Radius of curvature | Spacing | Refractive index | Abbe number vd |
|---|---|---|---|---|
| OBJ | INF | INF | 1. | |
| 1 | 4.6507 | 0.5827 | 1.88300 | 40.76 |
| 2$ | 0.9898 | 1.2497 | 1. | |
| 3 | −2.0555 | 0.8646 | 1.88300 | 40.76 |
| 4 | −36.6954 | 0.0236 | 1. | |
| STO | INF | 0.0238 | 1. | |
| 6 | 5.4583 | 2.7623 | 1.88300 | 40.76 |
| 7 | −2.3557 | 0.1165 | 1. | |
| 8 | 3.7377 | 1.6249 | 1.72916 | 54.68 |
| 9 | −1.9660 | 0.4661 | 2.14352 | 17.77 |
| 10$ | −8.9159 | 0.1515 | 1. | |
| 11 | INF | 0.6992 | 1.51800 | 75.00 |
| 12 | INF | 0.3711 | 1. | |
| 13 | INF | 1.1653 | 1.51633 | 64.14 |
| 14 | INF | 0.0117 | 1.51000 | 64.10 |
| 15 | INF | 1.1653 | 1.61061 | 50.20 |
| IMG | INF | 0. | | |
| S2 ASP | RDY | K | | |
| | 0.9898 | −0.9203 | | |
| AC2 | AC4 | AC6 | AC8 | AC10 |
| 0.0000E+00 | 7.5227E−02 | 7.5287E−03 | 9.7190E−02 | 0.0000E+00 |
| S10 ASP | RDY | K | | |
| | −8.9159 | 0. | | |
| AC2 | AC4 | AC6 | AC8 | AC10 |
| 0.0000E+00 | −9.3580E−04 | −9.3712E−04 | 0.0000E+00 | 0.0000E+00 |

EXAMPLE 14

Figure 34:
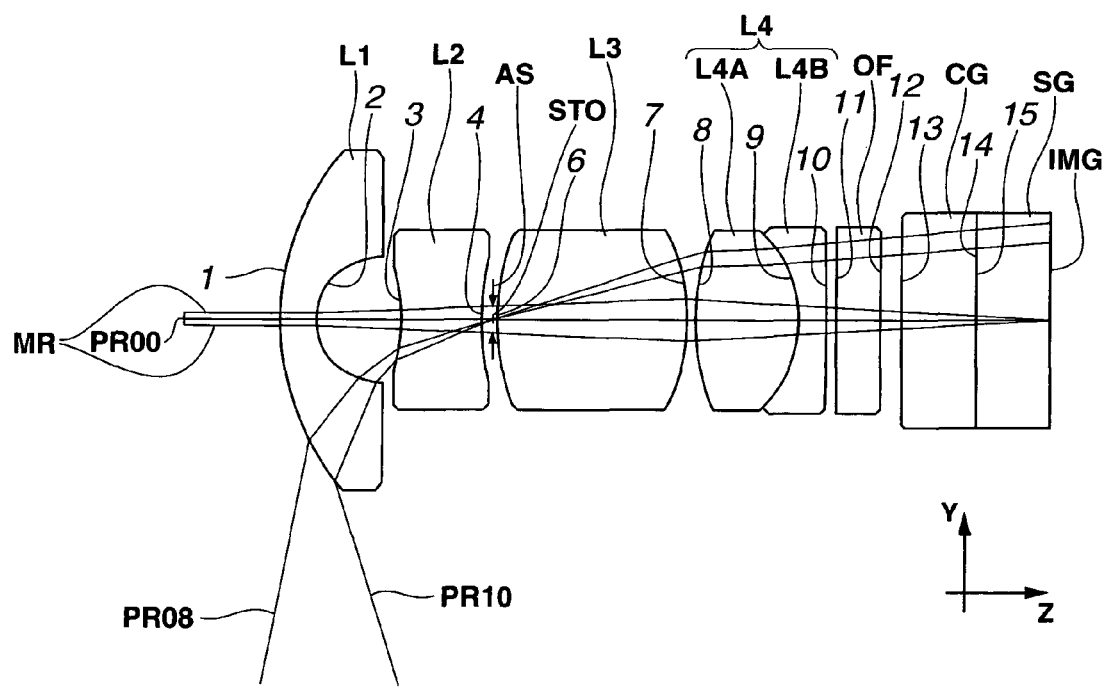
FIG. 34 is a drawing showing a configuration along an optical path of an optical system including the objective lens according to example 14 of the embodiment.
Figure 35:
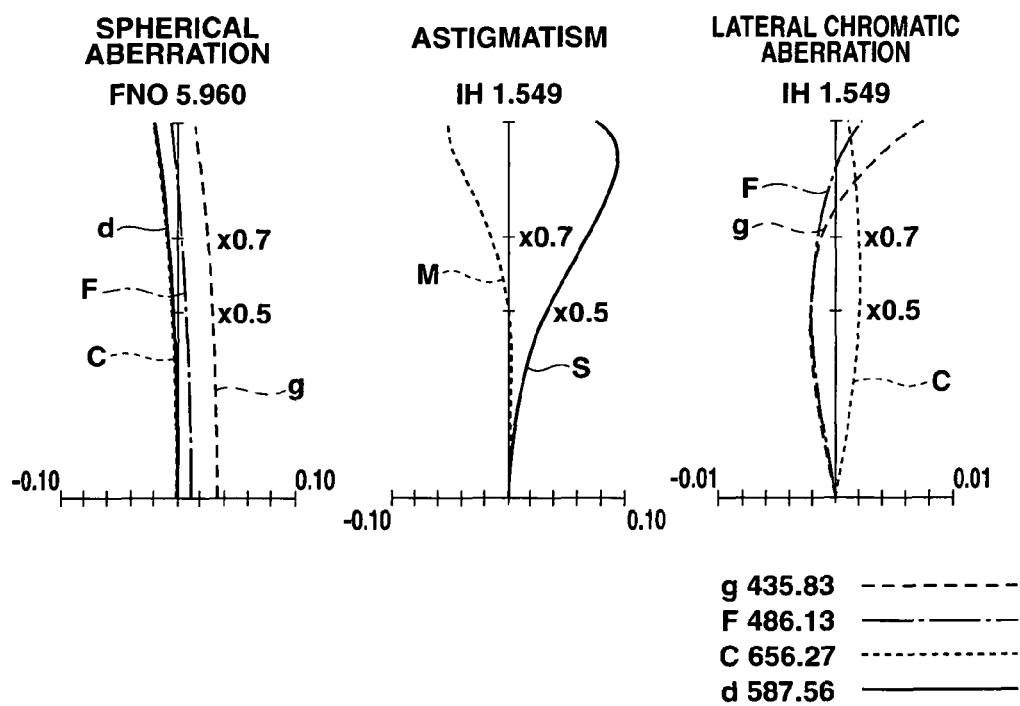
FIG. 35 is a drawing showing spherical aberration, astigmatism, and lateral chromatic aberration of the objective lens according to example 14 of the embodiment.

FIG. 34 is a drawing showing a configuration along the optical path of the optical system including the objective lens according to example 14 and FIG. 35 is a drawing showing spherical aberration, astigmatism, and lateral chromatic aberration of the objective lens according to example 14.

As shown in FIG. 34, the objective lens according to example 14 includes, in order from the object side, a first lens L1 which is a negative meniscus lens with a convex surface turned to the object side, a second lens L2 which is a double-concave lens (i.e., also a negative lens with a concave surface turned to the object side), an aperture stop AS, a third lens L3 which is a double-convex lens (positive lens), and a fourth lens L4 which is a cemented lens made up of a positive, double-convex lens L4A and a negative meniscus lens L4B with a convex surface turned to the image side. The negative lens L4B in the fourth lens L4 has an Abbe number (vd) of 18.90. The lenses L1 and L2 make up a front group with negative refractive power while lenses L3 and L4 make up a rear group with positive refractive power.

The objective lens according to example 14 has no aspherical surface. Surface No. 2 on the image side of the first lens L1 is spherical. On the outermost perimeter of surface No. 2, an angle formed by a normal to surface No. 2 and the optical axis is as large as almost 90°.

On the image side of the fourth lens L4, the above-described optical member OF, CCD cover glass CG, and CCD chip sealing glass SG are placed in order from the object side.

FIG. 34 shows rays including an axial marginal ray MR, a principal ray PR10 forming an image at a maximum angle of view at an image height ratio of 1 (an image height of 1.549), and a principal ray PR08 forming an image at an image height ratio of 0.8 (an image height of 1.549×0.8) as well as an optical axis PR00.

The spherical aberration, astigmatism, and lateral chromatic aberration are as shown in FIG. 35.

Numeric data of the optical system according to example 14 is shown below.

TABLE 14

| Surface number | Radius of curvature | Spacing | Refractive index | Abbe number vd |
| --- | --- | --- | --- | --- |
| OBJ | INF | INF | 1. | |
| 1 | 4.1149 | 0.5755 | 1.88300 | 40.76 |
| 2 | 1.0202 | 1.3160 | 1. | |
| 3 | −4.1343 | 1.3153 | 1.88300 | 40.76 |
| 4 | 6.1538 | 0.1637 | 1. | |
| STO | INF | 0.0674 | 1. | |
| 6 | 3.7741 | 2.9862 | 1.88300 | 40.76 |
| 7 | −3.1660 | 0.1151 | 1. | |
| 8 | 3.5610 | 1.6321 | 1.72916 | 54.68 |
| 9 | −1.9023 | 0.4604 | 1.92286 | 18.90 |
| 10 | −16.6915 | 0.1496 | 1. | |
| 11 | INF | 0.6906 | 1.51800 | 75.00 |
| 12 | INF | 0.3510 | 1. | |
| 13 | INF | 1.1510 | 1.51633 | 64.14 |
| 14 | INF | 0.0115 | 1.51000 | 64.10 |
| 15 | INF | 1.1510 | 1.61061 | 50.20 |
| IMG | INF | 0. | | |

Figure 36:
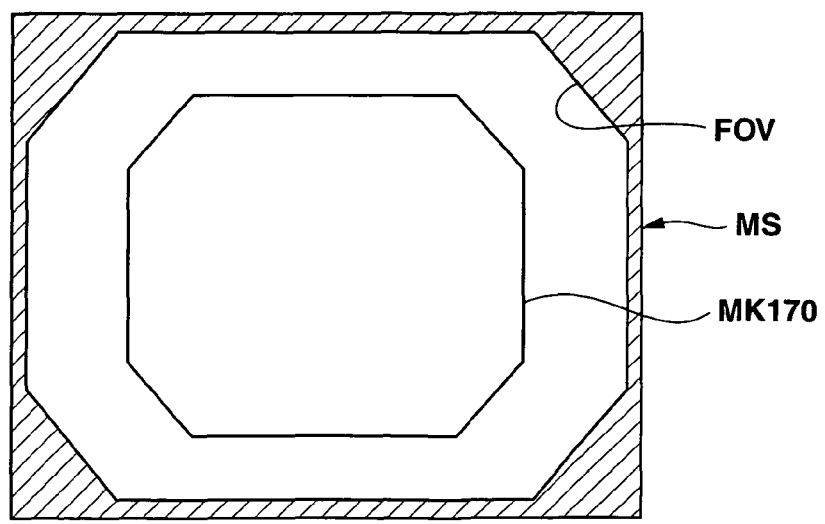
FIG. 36 is a drawing showing an example in which an index configured to identify an area covered by a 170° angle of view is displayed on an observation screen of an endoscope apparatus, according to the embodiment.
Figure 37:
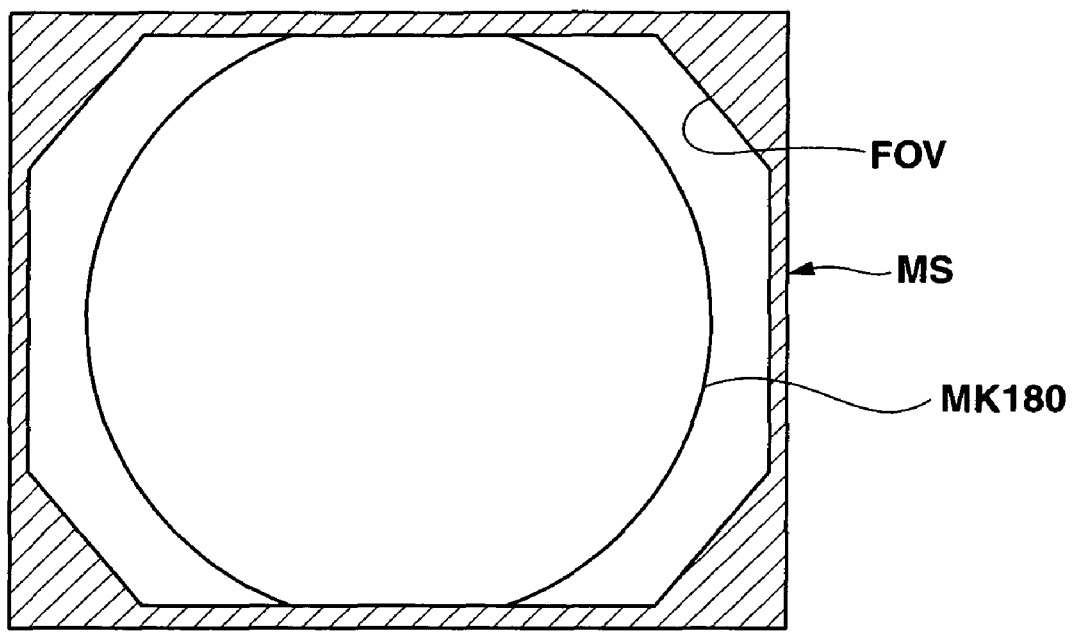
FIG. 37 is a drawing showing an example in which an index configured to identify an area covered by a 180° angle of view is displayed on the observation screen of the endoscope apparatus, according to the embodiment.

Furthermore, a configuration such as shown in FIG. 36 or 37 can be favorably applied to an endoscope apparatus which uses the objective lens according to the present embodiment. FIG. 36 is a drawing showing an example in which an index configured to identify an area covered by a 170° angle of view is displayed on an observation screen of the endoscope apparatus and FIG. 37 is a drawing showing an example in which an index configured to identify an area covered by a 180° angle of view is displayed on the observation screen of the endoscope apparatus.

That is, the objective lens according to the present embodiment has an angle of view of 180° or above, which is wider than in the case of conventional objective lenses (with an angle of view of 140° or 175°), and thus when the objective lens is applied to an endoscope apparatus, an index configured to identify the angle of view may be displayed on an observation screen of the endoscope apparatus in order to aid observation. The observation screen is, for example, a screen (an observation screen MS shown in FIGS. 36 and 37 by way of example) provided as a monitor screen (e.g., a TV screen) of the endoscope apparatus to allow observation of an image formed by the objective lens and picked up by an image pickup device or the like. However, the observation screen is not limited to this, and may be a screen configured to optically display an image formed by the objective lens and transmitted optically as required.

As an example of the index configured to aid observation, it is conceivable to display an index MK170 in an observation field of view FOV to indicate, for example, an area covered by a 170° angle of view which is the angle of view of a conventional endoscope, as shown in FIG. 36. This makes it possible to clearly recognize both the area covered by a 170° angle of view conventionally used for observation and an extra area newly available for observation.

Also, for example, an index MK180 which indicates an area covered by a 180° angle of view may be displayed in the observation field of view FOV as shown in FIG. 37. This makes it possible to clearly recognize a forward field of view and rearward field of view of an endoscope.

Examples of conceivable drawing methods for such an index include screen display which involves superimposing an index electrically generated by index generating means (an index generating unit) on an acquired endoscopic image. Regarding superimposition of the index, when the endoscopic image is an electronic image obtained as a result of image pickup, the index can be superimposed electrically, and when the endoscopic image is an optical image, an index generated electrically can be superimposed on the endoscopic image after being displayed optically. This technique has the advantage of being able to easily switch between displaying and hiding the index, switch among multiple types of index, or display multiple types of index simultaneously.

However, needless to say, index display is not limited to an electric one, and a technique for attaching an index to the optical system itself including the objective lens may be adopted alternatively. Concrete examples possibly include an example of attaching an index to the first lens L1 and an example of attaching an index to the optical member OF, the CCD cover glass CG, or the CCD chip sealing glass SG disposed near the image plane IMG. Furthermore, without limiting to these examples, the index may be displayed using another technique.

The embodiment described above provides a small, wide-angle objective lens with an angle of view of 180° or above suitable for an endoscope as well as an endoscope apparatus equipped with the objective lens.

It should be noted that the present invention is not limited to the precise embodiment described above and may be embodied by changing components in the implementation stage without departing from the spirit of the invention. Also, the invention can be implemented in various forms using appropriate combinations of the components disclosed in the above embodiment. For example, some of the components disclosed in the embodiment may be deleted. Furthermore, components may be combined as required across different embodiments. Thus, needless to say, various alterations and applications are possible without departing from the spirit of the invention.

What is claimed is:

1. An objective lens comprising, in order from an object side, a front group having negative refractive power, an aperture stop, and a rear group having positive refractive power, wherein:
    the front group comprises, in order from the object side, a first lens which is a negative meniscus lens with a convex surface turned to the object side and a second lens which is a negative lens with a concave surface turned to the object side;
    the rear group comprises, in order from the object side, a positive third lens and a fourth lens made up of a positive lens and a negative lens cemented together; and the objective lens satisfies conditional expression (1) below:

$$-0.8 < f\_F/f\_R < -0.3 \tag{1}$$

where
f_F is a focal length of the front group, and
f_R is a focal length of the rear group.

2. The objective lens according to claim 1, wherein the objective lens further satisfies conditional expressions (2) and (3) below:

$$-1.5 < f\_F/FL < -0.5. \quad (2)$$

$$1.7 < Fb/FL < 3.5 \quad (3)$$

where

FL is a focal length of an entire system, and

Fb is a back focus position (a distance from a surface of the fourth lens which is closest to an image side to a back focal point).

3. The objective lens according to claim 2, wherein the objective lens further satisfies conditional expressions (4) to (6) below:

$$-10 < r2a/FL < -2.5 \quad (4)$$

$$-0.5 < L\_enp/FL < 0.3 \quad (5)$$

$$vd < 20 \quad (6)$$

where r2a is a radius of curvature of an object-side surface of the second lens, L_enp is an entrance pupil position at a maximum angle of view (a distance from a first surface, where a direction toward the image side corresponds to a positive direction), and vd is an Abbe number of the negative lens in the fourth lens.

4. An endoscope apparatus comprising:

the objective lens according to claim 1; and an observation screen configured to display an image formed by the objective lens, wherein an index configured to identify an angle of view is displayed on the observation screen.

5. The endoscope apparatus according to claim 4, further comprising an index generating unit configured to electrically generate the index, wherein a display of the index on the observation screen is switchable between displaying and hiding the index.

* * * * *